(12) United States Patent
Grieger et al.

(10) Patent No.: US 9,441,206 B2
(45) Date of Patent: Sep. 13, 2016

(54) CELL LINE FOR PRODUCTION OF ADENO-ASSOCIATED VIRUS

(71) Applicant: The University of North Carolina at Chapel Hill, Chapel Hill, NC (US)

(72) Inventors: Joshua Grieger, Graham, NC (US); Richard Jude Samulski, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 14/354,634

(22) PCT Filed: Oct. 26, 2012

(86) PCT No.: PCT/US2012/062101
§ 371 (c)(1),
(2) Date: Apr. 28, 2014

(87) PCT Pub. No.: WO2013/063379
PCT Pub. Date: May 2, 2013

(65) Prior Publication Data
US 2014/0242671 A1    Aug. 28, 2014

Related U.S. Application Data

(60) Provisional application No. 61/552,492, filed on Oct. 28, 2011.

(51) Int. Cl.
*C12N 5/06* (2006.01)
*C12N 7/00* (2006.01)

(52) U.S. Cl.
CPC ....... *C12N 7/00* (2013.01); *C12N 2750/14151* (2013.01); *C12N 2750/14152* (2013.01)

(58) Field of Classification Search
None
See application file for complete search history.

(56) References Cited

U.S. PATENT DOCUMENTS

| | | | |
|---|---|---|---|
| 5,436,146 A | 7/1995 | Shenk et al. | |
| 6,146,874 A | 11/2000 | Zolotukhin et al. | |
| 2004/0197895 A1 | 10/2004 | Kotin et al. | |
| 2007/0202587 A1 | 8/2007 | Hwang et al. | |
| 2009/0275107 A1 | 11/2009 | Lock et al. | |

FOREIGN PATENT DOCUMENTS

| | | |
|---|---|---|
| EP | 0488528 A1 | 6/1992 |
| WO | WO 97/09441 A2 | 3/1997 |

OTHER PUBLICATIONS

Schoofs et al. A high-yielding serum-free, suspension cell culture process to manufacture recombinant adenoviral vectors for gene therapy. Cytotechnology. Nov. 1998;28(1-3):81-9.*
Johnson et al. Mutagenesis of adeno-associated virus type 2 capsid protein VP1 uncovers new roles for basic amino acids in trafficking and cell-specific transduction. J Virol. Sep. 2010;84(17):8888-902. Epub Jun. 23, 2010.*
Tsao et al. Development and improvement of a serum-free suspension process for the production of recombinant adenoviral vectors using HEK293 cells. Cytotechnology 37: 189-198, 2001.*
AAV-293 Cells, Catalog #240073, 2004, Retrieved from the Internet: URL:http://2010.igem.org/wiki/images/e/e0/Freiburg10_AAv293_cell_line 2 pages.
Durocher et al. "Scalable serum-free production of recombinant adeno-associated virus type 2 by transfection of 293 suspension cells", *J. Virological Methods* 144:32-40 (2007).
Gao et al. "Novel adeno-associated viruses from rhesus monkeys as vectors for human gene therapy", *PNAS* 99(18):11854-11859 (2002).
Halbert et al. "Capsid-expressing DNA in AAV vectors and its elimination by use of an oversize capsid gene for vector production", *Gene Ther.* 18(4):411-417 (2011).
Hildinger et al. "High-titer, serum-free production of adeno-associated virus vectors by polyethyleneimine-mediated plasmid transfection in mammalian suspension cells", *Biotechnol Lett* 29:1713-1721 (2007).
Lock et al. "Rapid, Simple, and Versatile Manufacturing of Recombinant Adeno-Associated Viral Vectors at Scale", *Human Gene Therapy* 21:1259-1271 (2010).
Park et al. "Scalable Production of Adeno-Associated Virus Type 2 Vectors Via Suspension Transfection", *Biotechnology and Bioengineering* 94(3):416-430 (2006).
Vandenberghe et al. "Efficient Serotype-Dependent Release of Functional Vector into the Culture Medium During Adeno-Associated Virus Manufacturing", *Human Gene Therapy* 21:1251-1257 (2010).
Xiao et al. "Production of High-Titer Recombinant Adeno-Associated Virus Vectors in the Absence of Helper Adenovirus", *J. Virology* 72 (3):2224-2232 (1998).
Wright "Transient Transfection Methods for Clinical Adeno-Associated Viral Vector Production", *Human Gene Therapy* 20:698-706 (2009).
Notification of Transmittal of the International Search Report and the Written Opinion of the International Searching Authority, or the Declaration corresponding to International Application No. PCT/US2012/062101 mailed Mar. 6, 2013.
Notification Concerning Transmittal of International Preliminary Report on Patentability corresponding to International Application No. PCT/US2012/062101 mailed May 8, 2014.
Extended European Search Report corresponding to European Application No. 12842892.7 issued Mar. 18, 2015.

* cited by examiner

*Primary Examiner* — Nick Zou
(74) *Attorney, Agent, or Firm* — Myers Bigel & Sibley, P.A.

(57) ABSTRACT

This invention relates to a HEK293 cell line that grows under animal component-free suspension conditions. The cell line is ideal for rapid and scalable production of adeno-associated virus (AAV) and supports production of all serotypes and chimera of AAV.

1 Claim, 10 Drawing Sheets

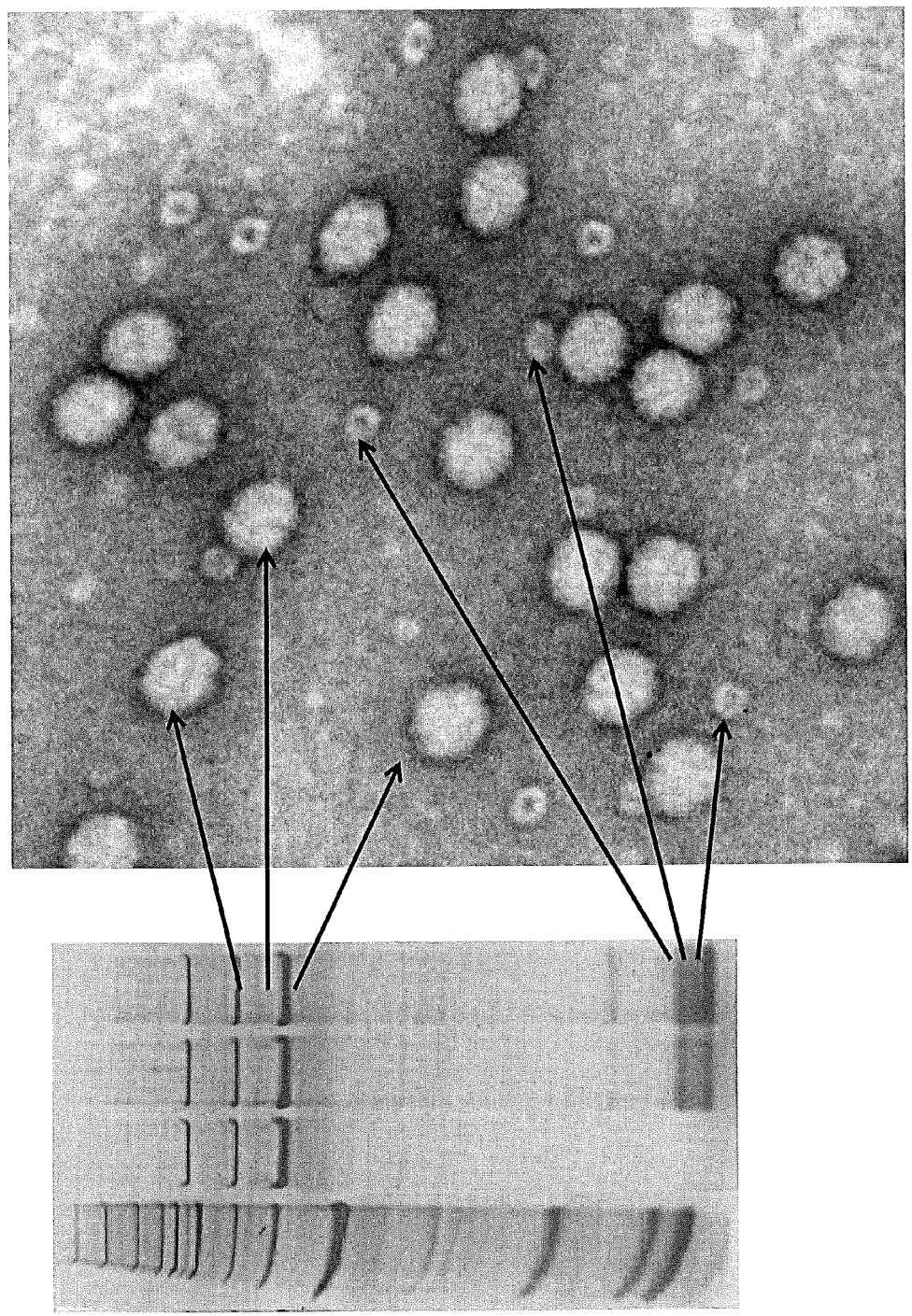

| Serotype | Single-stranded | | | Self-complementary | | |
|---|---|---|---|---|---|---|
| | Full | Empty | Ratio F:E | Full | Empty | Ratio F:E |
| 1 | 151 | 5 | 30.2 | 298 | 3 | 99.3 |
| 2 | 289 | 11 | 26.3 | 608 | 14 | 43.4 |
| 3 | 258 | 24 | 10.8 | 549 | 46 | 11.9 |
| 4 | 64 | 1 | 64.0 | 42 | 3 | 14.0 |
| 5 | 199 | 11 | 18.1 | 486 | 23 | 21.1 |
| 6 | 240 | 6 | 40.0 | 240 | 7 | 34.3 |
| 8 | 409 | 3 | 136.3 | 289 | 28 | 10.3 |
| 9 | 570 | 25 | 22.8 | 252 | 8 | 31.5 |

US 9,441,206 B2

CELL LINE FOR PRODUCTION OF ADENO-ASSOCIATED VIRUS

RELATED APPLICATIONS

This application is a 35 U.S.C. §371 national phase application of PCT Application PCT/US2012/062101, filed Oct. 26, 2012, which claims the benefit of U.S. Provisional Application Ser. No. 61/552,492, filed Oct. 28, 2011. The entire contents of each of these applications is fully incorporated herein by reference.

FIELD OF THE INVENTION

This invention relates to a HEK293 cell line that grows in animal component-free suspension conditions. The cell line is ideal for rapid and scalable production of adeno-associated virus (AAV) and supports production of all serotypes and chimera of AAV.

BACKGROUND OF THE INVENTION

Recombinant adeno-associated virus (rAAV) vectors have demonstrated transduction and long-term gene expression with little to no toxicity and inflammation in vivo. These unique characteristics of AAV have led to its recognition as a leading vector candidate for gene therapy applications. A number of Phase I and Phase II clinical trials utilizing AAV have been performed worldwide (Aucoin et al., Biotechnol. Adv. 26:73 (2008); Mueller et al., Gene Ther. 15:858 (2008)). However, many preclinical studies and successful clinical trials have demonstrated a number of challenges that will need to be addressed to sustain rAAV use for human gene therapy (Mueller et al., Gene Ther. 15:858 (2008)). One major challenge is establishing large scale manufacturing technologies in accordance with current Good Manufacturing Practices (cGMP) to yield the purified vector quantities needed for the expanding clinical need. The success of generating a scalable production technology relies heavily on understanding the basic biology of AAV in regard to generating reagents such as cell lines, plasmids or recombinant viral vectors, etc. that when used together, will closely mimic wild-type AAV production.

AAV has been classified as a *dependovirus* in the Parvovirus family because it requires coinfection with helper viruses such as adenovirus (Ad) or herpes simplex virus (HSV) for productive infection in cell culture (Atchison et al., Science 149:754 (1965); Buller et al., J. Virol. 40:241 (1981)). Parvoviruses are among the smallest of the DNA animal viruses with a virion of approximately 25 nm in diameter composed entirely of protein and DNA. The AAV genome is a linear, single-stranded DNA molecule containing 4679 bases (Srivastava et al., Virol. 45:555 (1983)). The wild-type (wt) AAV genome is made up of two genes that encode four replication proteins and three capsid proteins, respectively, and are flanked on either end by inverted terminal repeats (ITRs) (Lusby et al., J. Virol. 4:402 (1980); Srivastava et al., J. Virol. 45:555 (1983)). The ITRs are the only cis-acting elements necessary for genome replication and packaging into the capsid. The four replication proteins (Rep 78, 68, 52 and 40) are multifunctional and play a role in transcription, viral DNA replication and DNA packaging into the preformed viral capsid within the nucleus of the infected cell (Chejanovsky et al., Virology 173:120 (1989); King et al., EMBO J. 20:3282 (2001)). The viral capsid is made up of the three proteins Vp1, Vp2 and Vp3 in a ratio of 1:1:8 respectively. The capsid proteins are produced from the same open reading frame (ORF) but utilize different translational start sites.

Because the ITRs are the only cis acting elements necessary for genome replication and packaging, the rep and cap genes can be removed and cloned into a separate plasmid without a loss in function. A promoter and gene of interest driven by a promoter can then be cloned between the ITRs. Thus any gene that is flanked by the ITRs can effectively be packaged into an AAV capsid as long as the genome is smaller than 5.0 kb in size (Dong et al., Mol. Ther. 18:87 (2010); Grieger et al., J. Virol. 79:9933 (2005); Wu et al., Mol. Ther. 18:80 (2010)). However, AAV still lacks the ability to replicate. One of the distinctive features of AAV is the requirement of co-infection with a helper virus such as Ad or HSV. The generation of rAAV used to require transfection of the vector and packaging constructs into Ad-infected cells (Muzyczka, Curr. Top. Microbiol. Immunol. 158:97 (1992)). Upon co-infection with Ad or HSV, AAV utilizes several helper virus early genes to facilitate its own replication. Infection of Ad into producer cells to generate rAAV was effective in producing rAAV, but a consequence was that it also produced overabundant Ad particles. Complete removal of Ad has relied on physical techniques such as CsCl gradients, column chromatography, and a heat-denaturing step to inactivate any residual Ad particles that may still be present. While most of these procedures have succeeded to various degrees, the potential for Ad contamination is an unwanted risk and the presence of Ad denatured proteins is unacceptable for clinical use. A significant improvement in the evolution of rAAV production was the introduction of the triple plasmid transfection (Xiao et al., J. Virol. 72:2224 (1998)). This method used a variation of the rep and cap plasmid as well as the ITR plasmid, but eliminated the use of Ad infection. The Ad proteins of E1A, E1B, E4 and E2A and VA RNA were cloned into a single plasmid called XX680. Supplying the Ad helper genes on the XX680 plasmid eliminated Ad production in the transfected cells yielding only rAAV vector. The triple transfection method remains a standard production method in most laboratories experimenting with rAAV. However, this method has been limited to the use of adherent cells.

Advances in rAAV production have been made in the past 10 years that have allowed a number of laboratories to move away from production using adherent HEK293 cells and move toward scalable technologies such as infection-based technologies through the use of recombinant adenovirus (Gao et al., Mol. Ther. 5:644 (2002); Gao et al., Hum. Gene Ther. 9:2353 (1998); Liu et al., Mol. Ther. 2:394 (2000); Liu et al., Gene Ther. 6:293 (1999); Tessier et al., J. Virol. 75:375 (2001)), herpes simplex virus (Booth et al., Gene Ther. 11:829 (2004); Conway et al., Gene Ther. 6:986 (1999); Hwang et al., Mol. Ther. 7:S14 (2003); Kang et al., Gene Ther. 16:229 (2009); Thomas et al., Hum. Gene Ther. 20:861 (2009)), baculovirus expression vector system (BEVS) (Aslanidi et al., Proc. Natl. Acad. Sci. USA 106:5059 (2009); Cecchini et al., Gene Ther. 15:823 (2008); Kohlbrenner et al., Mol. Ther. 12:1217 (2005); Negrete et al., Meth. Mol. Biol. 433:79 (2008); Negrete et al., J. Gene Med. 9:938 (2007); Urabe et al., Hum. Gene Ther. 13:1935 (2002); Urabe et al., J. Virol. 80:1874 (2006)), and transient transfection of suspension HEK293 cells (Durocher et al., J. Virol. Meth. 144:32 (2007); Hildinger et al., Biotechnol. Lett. 29:1713 (2007); Park et al., Biotechnol. Bioeng. 94:416 (2006)). Park et al. and Durocher et al. demonstrated that approximately $1.4 \times 10^4$ and $3 \times 10^4$ vg/cell, respectively, were generated using their optimized serum-free suspension HEK293 cell production systems. Common with these studies is the fact that the yield of vector continues to be the impediment and is significantly below the vg/cell generated via transfection of adherent HEK293 cells and the rHSV production system.

Cesium chloride purification (CsCl) is still the most widely used form of AAV purification (Grieger et al., *Nat. Protoc.* 1:1412 (2006); Grieger et al., *Adv. Biochem. Eng. Biotechnol.* 99:119 (2005)). The benefits of using CsCl purification are its relative low cost, compatibility for any AAV serotype and separation of empty and genome containing particles. However, several drawbacks detract from this method being used for clinical applications including: (1) the time and effort required to identify the virus containing fractions within multiple CsCl gradient purification runs; (2) the resulting virus containing many impurities in addition to cesium; (3) impediments with scaling up; and (4) numerous open steps during purification (Brument et al., *Mol. Ther.* 6:678 (2002); Chahal et al., *J. Virol. Meth.* 139:61 (2007); Hermens et al., *Hum. Gene Ther.* 10:1885 (1999); Kaludov et al., *Hum. Gene Ther.* 13:1235 (2002); Smith et al., *J. Virol. Meth.* 114:115 (2003); Zolotukhin, *Hum. Gene Ther.* 16:551 (2005)). Experiments conducted by Hermens et al. and Zolotukhin et al. showed that a density gradient medium called iodixanol was very effective in isolating AAV2 after further purification using heparin affinity chromatography (Hermens et al., *Hum. Gene Ther.* 10:1885 (1999); Zolotukhin et al., *Gene Ther.* 6:973 (1999); Zolotukhin et al., *Methods* 28:158 (2002)). The caveat of this system was the inability to purify other AAV serotypes and chimeric capsids lacking affinity for heparin sulfate, thus reverting purification of rAAV to CsCl. There have been several other attempts at purification without the use of CsCl including the manipulation of the viral capsids with epitopes (Koerber et al., *Hum. Gene Ther.* 18:367 (2007)) and various forms of chromatography (Brument et al., *Mol. Ther.* 6:678 (2002); Chahal et al., *J. Virol. Meth.* 139:61 (2007); Davidoff et al., *J. Virol. Meth.* 121:209 (2004); Gao et al., *Hum. Gene Ther.* 11:2079 (2000); Hermens et al., *Hum. Gene Ther.* 10:1885 (1999); Kaludov et al., *Hum. Gene Ther.* 13:1235 (2002); Smith et al., *J. Virol. Meth.* 114:115 (2003); Zolotukhin et al., *Gene Ther.* 6:973 (1999); Zolotukhin et al., *Methods* 28:158 (2002)). The use of ion exchange chromatography has been shown to successfully purify several AAV serotypes. Brument et al. and Davidoff et al. used a two column system to purify AAV serotypes 2, 5 and 8 (Brument et al., *Mol. Ther.* 6:678 (2002); Davidoff et al., *J. Virol. Meth.* 121:209 (2004)). Zolotukhin et al. showed that use of iodixanol in addition to ion exchange utilizing a Q-Sepharose column was able to purify serotypes 1, 2, and 5 (Zolotukhin et al., *Methods* 28:158 (2002)). These methods showed great promise in AAV purification, but were only effective on the serotypes specified. A universal method has yet to be identified that can purify all serotypes of AAV.

The present invention provides a HEK293 cell line that grows under animal component-free suspension conditions and can be used in an AAV production system that is rapid, scalable, produces high titers, and functions with all serotypes and chimeras of AAV.

SUMMARY OF THE INVENTION

The present invention relates to the development of a scalable manufacturing process for AAV vectors that efficiently generates high titer, highly pure, and potent quantities of AAV vectors. Development of the process included the generation of a HEK293 cell line that grows under animal component-free suspension conditions.

One aspect of the invention relates to an isolated HEK293 cell deposited as ATCC No. PTA 13274.

Another aspect of the invention relates to a method of producing AAV particles, comprising: (a) providing to the HEK293 cells of the invention an AAV expression system; (b) culturing the cells under conditions in which AAV particles are produced; and (c) optionally isolating the AAV particles.

These and other aspects of the invention are set forth in more detail in the description of the invention below.

BRIEF DESCRIPTION OF THE DRAWINGS

FIGS. 3A-3B illustrates the purity of the elution peak fractions of AAV after column chromatography via silver stain and negative stain transmission electron microscopy (TEM).

DETAILED DESCRIPTION OF THE INVENTION

Figure 1:
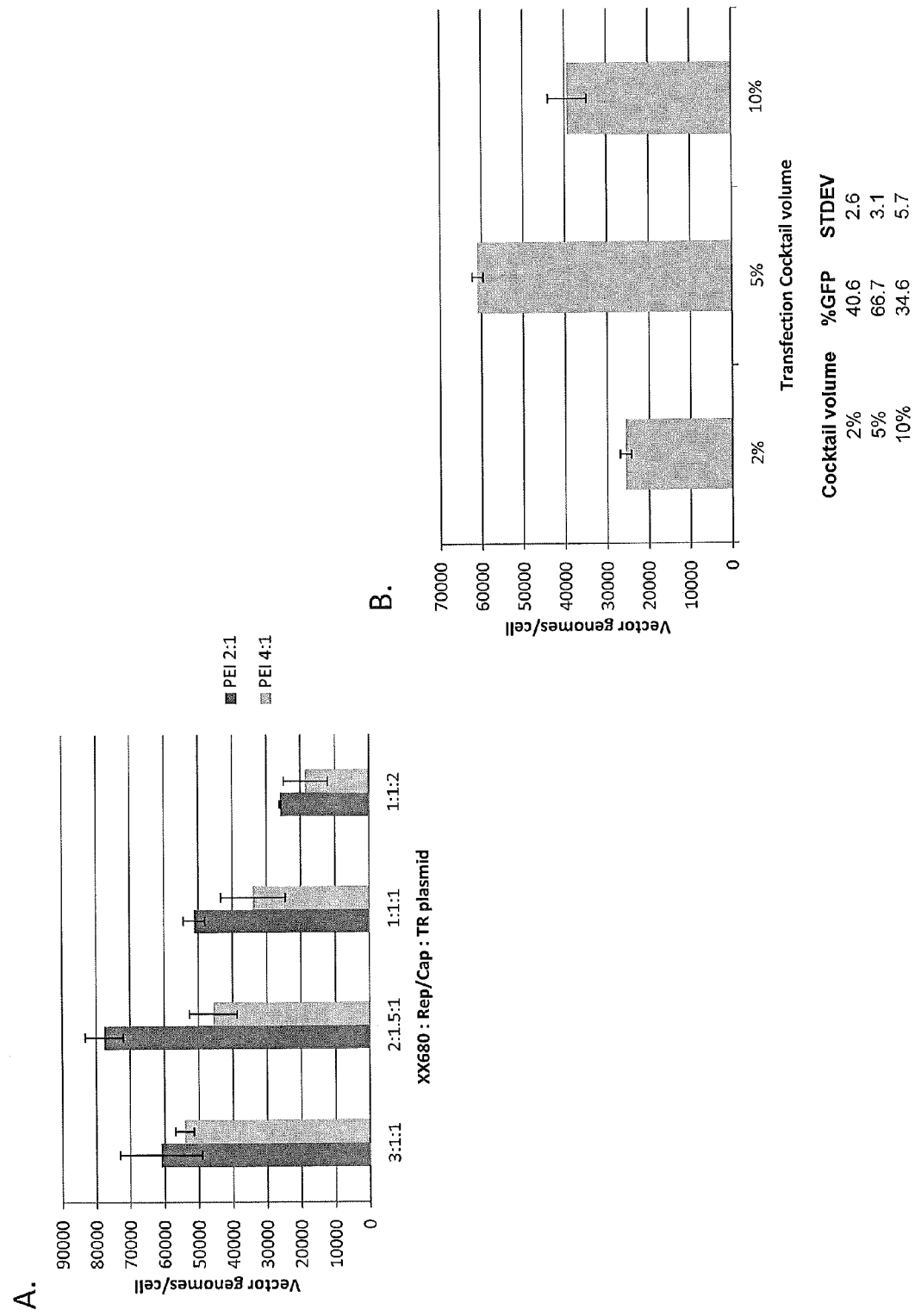
FIGS. 1A-1B show the optimization of triple transfection plasmid ratios and transfection cocktail volumes. (A) Varying plasmid ratios of XX680, AAV rep/cap helper and TR plasmid were explored to determine the optimal plasmid ratio for rAAV vector production. (B) Varying transfection cocktail volumes were tested to determine optimal transfection conditions with a transfection reagent (chemical or lipid) to DNA ratio of 2:1 and an incubation time. Percent volume of transfection cocktail is in reference to percent of final cell culture volume.

The present invention will now be described with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 CFR §1.822 and established usage. See, e.g., *PatentIn User Manual*, 99-102 (November 1990) (U.S. Patent and Trademark Office).

Except as otherwise indicated, standard methods known to those skilled in the art may be used for the construction of rAAV constructs, packaging vectors expressing the AAV Rep and/or Cap sequences, and transiently and stably transfected packaging cells. Such techniques are known to those skilled in the art. See, e.g., SAMBROOK et al. MOLECULAR CLONING: A LABORATORY MANUAL 2nd Ed. (Cold Spring Harbor, N.Y., 1989); AUSUBEL et al. CURRENT PROTOCOLS IN MOLECULAR BIOLOGY (Green Publishing Associates, Inc. and John Wiley & Sons, Inc., New York).

Moreover, the present invention also contemplates that in some embodiments of the invention, any feature or combination of features set forth herein can be excluded or omitted.

DEFINITIONS

The following terms are used in the description herein and the appended claims:

The singular forms "a" and "an" are intended to include the plural forms as well, unless the context clearly indicates otherwise.

Furthermore, the term "about," as used herein when referring to a measurable value such as an amount of the length of a polynucleotide or polypeptide sequence, dose, time, temperature, and the like, is meant to encompass variations of 20%, 10%, 5%, 1%, 0.5%, or even 0.1% of the specified amount.

Also as used herein, "and/or" refers to and encompasses any and all possible combinations of one or more of the associated listed items, as well as the lack of combinations when interpreted in the alternative ("or").

As used herein, the transitional phrase "consisting essentially of" is to be interpreted as encompassing the recited materials or steps "and those that do not materially affect the basic and novel characteristic(s)" of the claimed invention (e.g., rAAV replication). See, *In re Herz*, 537 F.2d 549, 551-52, 190 U.S.P.Q. 461, 463 (CCPA 1976) (emphasis in the original); see also MPEP §2111.03. Thus, the term "consisting essentially of" as used herein should not be interpreted as equivalent to "comprising."

The term "parvovirus" as used herein encompasses the family Parvoviridae, including autonomously-replicating parvoviruses and dependoviruses. The autonomous parvoviruses include members of the genera *Parvovirus, Erythrovirus, Densovirus, Iteravirus,* and *Contravirus*. Exemplary autonomous parvoviruses include, but are not limited to, minute virus of mouse, bovine parvovirus, canine parvovirus, chicken parvovirus, feline panleukopenia virus, feline parvovirus, goose parvovirus, H1 parvovirus, muscovy duck parvovirus, snake parvovirus, and B19 virus. Other autonomous parvoviruses are known to those skilled in the art. See, e.g., FIELDS et al. VIROLOGY, volume 2, chapter 69 (4th ed., Lippincott-Raven Publishers).

The genus *Dependovirus* contains the adeno-associated viruses (AAV), including but not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, avian AAV, bovine AAV, canine AAV, goat AAV, snake AAV, equine AAV, and ovine AAV. See, e.g., FIELDS et al. VIROLOGY, volume 2, chapter 69 (4th ed., Lippincott-Raven Publishers); and Table 1.

As used herein, the term "adeno-associated virus" (AAV), includes but is not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, snake AAV, avian AAV, bovine AAV, canine AAV, equine AAV, ovine AAV, goat AAV, shrimp AAV, and any other AAV now known or later discovered. See, e.g., FIELDS et al. VIROLOGY, volume 2, chapter 69 (4th ed., Lippincott-Raven Publishers). A number of relatively new AAV serotypes and clades have been identified (See, e.g., Gao et al., *J. Virol.* 78:6381 (2004); Moris et al., *Virol.* 33:375 (2004); and Table 1).

TABLE 1

| Complete Genomes | GenBank Accession Number | | GenBank Access. No. | | GenBank Access. No. |
|---|---|---|---|---|---|
| Adeno-associated virus 1 | NC_002077, AF063497 | Hu T88 | AY695375 | Hu42 | AY530605 |
| Adeno-associated virus 2 | NC_001401 | Hu T71 | AY695374 | Hu67 | AY530627 |
| Adeno-associated virus 3 | NC_001729 | Hu T70 | AY695373 | Hu40 | AY530603 |
| Adeno-associated virus 3B | NC_001863 | Hu T40 | AY695372 | Hu41 | AY530604 |

TABLE 1-continued

| Complete Genomes | GenBank Accession Number | | GenBank Access. No. | | GenBank Access. No. |
|---|---|---|---|---|---|
| Adeno-associated virus 4 | NC_001829 | Hu T32 | AY695371 | Hu37 | AY530600 |
| Adeno-associated virus 5 | Y18065, AF085716 | Hu T17 | AY695370 | Rh40 | AY530559 |
| Adeno-associated virus 6 | NC_001862 | Hu LG15 | AY695377 | Rh2 | AY243007 |
| Avian AAV ATCC VR-865 | AY186198, AY629583 | Clade C | | Bb1 | AY243023 |
| | NC_004828 | Hu9 | AY530629 | Bb2 | AY243022 |
| Avian AAV strain DA-1 | NC_006263, AY629583 | Hu10 | AY530576 | Rh10 | AY243015 |
| Bovine AAV | NC_005889, AY388617 | Hu11 | AY530577 | Hu17 | AY530582 |
| Clade A | | Hu53 | AY530615 | Hu6 | AY530621 |
| AAV1 | NC_002077, AF063497 | Hu55 | AY530617 | Rh25 | AY530557 |
| AAV6 | NC_001862 | Hu54 | AY530616 | Pi2 | AY530554 |
| Hu. 48 | AY530611 | Hu7 | AY530628 | Pi1 | AY530553 |
| Hu 43 | AY530606 | Hu18 | AY530583 | Pi3 | AY530555 |
| Hu 44 | AY530607 | Hu15 | AY530580 | Rh57 | AY530569 |
| Hu 46 | AY530609 | Hu16 | AY530581 | Rh50 | AY530563 |
| Clade B | | Hu25 | AY530591 | Rh49 | AY530562 |
| Hu. 19 | AY530584 | Hu60 | AY530622 | Hu39 | AY530601 |
| Hu. 20 | AYS30586 | Ch5 | AY243021 | Rh58 | AY530570 |
| Hu23 | AY530589 | Hu3 | AY530595 | Rh61 | AY530572 |
| Hu22 | AY530588 | Hu1 | AY530575 | Rh52 | AY530565 |
| Hu24 | AY530590 | Hu4 | AY530602 | Rh53 | AY530566 |
| Hu21 | AY530587 | Hu2 | AY530585 | Rh51 | AY530564 |
| Hu27 | AY530592 | Hu61 | AY530623 | Rh64 | AY530574 |
| Hu28 | AY530593 | Clade D | | Rh43 | AY530560 |
| Hu 29 | AY530594 | Rh62 | AY530573 | AAV8 | AF513852 |
| Hu63 | AY530624 | Rh48 | AY530561 | Rh8 | AY242997 |
| Hu64 | AY530625 | Rh54 | AY530567 | Rh1 | AY530556 |
| Hu13 | AY530578 | Rh55 | AY530568 | Clade F | |
| Hu56 | AY530618 | Cy2 | AY243020 | Hu14 (AAV9) | AY530579 |
| Hu57 | AY530619 | AAV7 | AF513851 | Hu31 | AY530596 |
| Hu49 | AY530612 | Rh35 | AY243000 | Hu32 | AY530597 |
| Hu58 | AY530620 | Rh37 | AY242998 | Clonal Isolate | |
| Hu34 | AY530598 | Rh36 | AY242999 | AAV5 | Y18065, AF085716 |
| Hu35 | AY530599 | Cy6 | AY243016 | AAV 3 | NC_001729 |
| AAV2 | NC_001401 | Cy4 | AY243018 | AAV 3B | NC_001863 |
| Hu45 | AY530608 | Cy3 | AY243019 | AAV4 | NC_001829 |
| Hu47 | AY530610 | Cy5 | AY243017 | Rh34 | AY243001 |
| Hu51 | AY530613 | Rh13 | AY243013 | Rh33 | AY243002 |
| Hu52 | AY530614 | Clade E | | Rh32 | AY243003 |
| Hu T41 | AY695378 | Rh38 | AY530558 | | |
| Hu S17 | AY695376 | Hu66 | AY530626 | | |

The genomic sequences of various serotypes of AAV, as well as the sequences of the native ITRs, Rep proteins, and capsid subunits are known in the art. Such sequences may be found in the literature or in public databases such as GenBank. See, e.g., GenBank Accession Numbers NC_002077, NC_001401, NC_001729, NC_001863, NC_001829, NC_001862, NC_000883, NC_001701, NC_001510, NC_006152, NC_006261, AF063497, U89790, AF043303, AF028705, AF028704, J02275, J01901, J02275, X01457, AF288061, AH009962, AY028226, AY028223, AY631966, AX753250, EU285562, NC_001358, NC_001540, AF513851, AF513852 and AY530579; the disclosures of which are incorporated by reference herein for teaching AAV nucleic acid and amino acid sequences. See also, e.g., Bantel-Schaal et al., *J. Virol.* 73:939 (1999); Chiorini et al., *J. Virol.* 71:6823 (1997); Chiorini et al., *J. Virol.* 73:1309 (1999); Gao et al., *Proc. Nat. Acad. Sci. USA* 99:11854 (2002); Moris et al., *Virology,* 33:375 (2004); Mori et al., *Virology,* 330:375 (2004); Muramatsu et al., *Virology,* 221: 208 (1996); Ruffing et al., *J. Gen. Virol.* 75:3385 (1994); Rutledge et al., *J. Virol.* 72:309 (1998); Schmidt et al., *J. Virol.* 82:8911 (2008); Shade et al., *J. Virol.* 58:921 (1986); Srivastava et al., *J. Virol.* 45:555 (1983); Xiao et al., *J. Virol.* 73:3994 (1999); international patent publications WO 00/28061, WO 99/61601, WO 98/11244; and U.S. Pat. No. 6,156,303; the disclosures of which are incorporated by reference herein for teaching AAV nucleic acid and amino acid sequences. See also Table 1. An early description of the AAV1, AAV2 and AAV3 ITR sequences is provided by Xiao, X., (1996), "Characterization of Adeno-associated virus (AAV) DNA replication and integration," Ph.D. Dissertation, University of Pittsburgh, Pittsburgh, Pa. (incorporated herein it its entirety).

The term "tropism" as used herein refers to entry of the virus into the cell, optionally and preferably followed by expression (e.g., transcription and, optionally, translation) of sequences carried by the viral genome in the cell, e.g., for a recombinant virus, expression of the heterologous nucleotide sequences(s). Those skilled in the art will appreciate that transcription of a heterologous nucleic acid sequence from the viral genome may not be initiated in the absence of trans-acting factors, e.g., for an inducible promoter or otherwise regulated nucleic acid sequence. In the case of AAV, gene expression from the viral genome may be from a stably integrated provirus, from a non-integrated episome, as well as any other form in which the virus may take within the cell.

As used herein, "transduction" or "infection" of a cell by an AAV means that the AAV enters the cell to establish an active (i.e., lytic) infection. As used herein, "transduction" of a cell by AAV means that the AAV enters the cell to establish a latent infection. See, e.g., FIELDS et al. VIROLOGY, volume 2, chapter 69 (4th ed., Lippincott-Raven Publishers).

The terms "5' portion" and "3' portion" are relative terms to define a spatial relationship between two or more elements. Thus, for example, a "3' portion" of a polynucleotide indicates a segment of the polynucleotide that is downstream of another segment. The term "3' portion" is not intended to indicate that the segment is necessarily at the 3' end of the polynucleotide, or even that it is necessarily in the 3' half of the polynucleotide, although it may be. Likewise, a "5' portion" of a polynucleotide indicates a segment of the polynucleotide that is upstream of another segment. The term "5' portion" is not intended to indicate that the segment is necessarily at the 5' end of the polynucleotide, or even that it is necessarily in the 5' half of the polynucleotide, although it may be.

As used herein, the term "polypeptide" encompasses both peptides and proteins, unless indicated otherwise.

A "polynucleotide" is a sequence of nucleotide bases, and may be RNA, DNA or DNA-RNA hybrid sequences (including both naturally occurring and non-naturally occurring nucleotide), and can be either single or double stranded DNA sequences.

As used herein, an "isolated" polynucleotide (e.g., an "isolated DNA" or an "isolated RNA") means a polynucleotide separated or substantially free from at least some of the other components of the naturally occurring organism or virus, for example, the cell or viral structural components (e.g., cell wall or cell membrane) or other polypeptides or nucleic acids commonly found associated with the polynucleotide. In some embodiments, an isolated polynucleotide is one that is at least about 20% pure, e.g., at least about 30, 40, 50, 60, 70, 80, 90, or 95% pure.

Likewise, an "isolated" polypeptide means a polypeptide that is separated or substantially free from at least some of the other components of the naturally occurring organism or virus, for example, the cell or viral structural components (e.g., cell wall or cell membrane) or other polypeptides or nucleic acids commonly found associated with the polypeptide. In some embodiments, an isolated polypeptide is one that is at least about 20% pure, e.g., at least about 30, 40, 50, 60, 70, 80, 90, or 95% pure.

A "therapeutic polypeptide" is a polypeptide that may alleviate or reduce symptoms that result from an absence or defect in a protein in a cell or subject. Alternatively, a "therapeutic polypeptide" is one that otherwise confers a benefit to a subject, e.g., anti-cancer effects or improvement in transplant survivability.

As used herein, the term "modified," as applied to a polynucleotide or polypeptide sequence, refers to a sequence that differs from a wild-type sequence due to one or more deletions, additions, substitutions, or any combination thereof.

As used herein, by "isolate" or "purify" (or grammatical equivalents) a virus vector, it is meant that the virus vector is at least partially separated from at least some of the other components in the starting material.

By the terms "treat," "treating" or "treatment of" (and grammatical variations thereof) it is meant that the severity of the subject's condition is reduced, at least partially improved or stabilized and/or that some alleviation, mitigation, decrease or stabilization in at least one clinical symptom is achieved and/or there is a delay in the progression of the disease or disorder.

The terms "prevent," "preventing" and "prevention" (and grammatical variations thereof) refer to prevention and/or delay of the onset of a disease, disorder and/or a clinical symptom(s) in a subject and/or a reduction in the severity of the onset of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset is less than what would occur in the absence of the present invention.

A "treatment effective" amount as used herein is an amount that is sufficient to provide some improvement or benefit to the subject. Alternatively stated, a "treatment effective" amount is an amount that will provide some alleviation, mitigation, decrease or stabilization in at least one clinical symptom in the subject. Those skilled in the art will appreciate that the therapeutic effects need not be complete or curative, as long as some benefit is provided to the subject.

A "prevention effective" amount as used herein is an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the invention. Those skilled in the art will appreciate that the level of prevention need not be complete, as long as some benefit is provided to the subject.

The terms "heterologous nucleotide sequence" and "heterologous nucleic acid" are used interchangeably herein and refer to a sequence that is not naturally occurring in the virus. Generally, the heterologous nucleic acid comprises an open reading frame that encodes a polypeptide or nontranslated RNA of interest (e.g., for delivery to a cell or subject).

As used herein, the terms "virus vector," "vector" or "gene delivery vector" refer to a virus (e.g., AAV) particle that functions as a nucleic acid delivery vehicle, and which comprises the vector genome (e.g., viral DNA [vDNA]) packaged within a virion. Alternatively, in some contexts, the term "vector" may be used to refer to the vector genome/vDNA alone.

The virus vectors of the invention can further be duplexed AAV particles as described in international patent publication WO 01/92551 (the disclosure of which is incorporated herein by reference in its entirety). Thus, in some embodiments, double stranded (duplex) genomes can be packaged into the virus capsids.

A "rAAV vector genome" or "rAAV genome" is an AAV genome (i.e., vDNA) that comprises one or more heterologous nucleic acid sequences. rAAV vectors generally require only the 145 base ITR in cis to generate virus. All other viral sequences are dispensable and may be supplied in trans (Muzyczka, Curr. Topics Microbiol. Immunol. 158:97 (1992)). Typically, the rAAV vector genome will only retain the one or more ITR sequence so as to maximize the size of the transgene that can be efficiently packaged by the vector. The structural and non-structural protein coding sequences may be provided in trans (e.g., from a vector, such as a plasmid, or by stably integrating the sequences into a packaging cell). In embodiments of the invention the rAAV vector genome comprises at least one ITR sequence (e.g., AAV ITR sequence), optionally two ITRs (e.g., two AAV ITRs), which typically will be at the 5' and 3' ends of the vector genome and flank the heterologous nucleic acid, but need not be contiguous thereto. The ITRs can be the same or different from each other.

An "AAV expression system" is a system of one or more polynucleotides that are sufficient, when introduced into a suitable host cell, to support production of rAAV. An AAV expression system will typically include polynucleotides encoding AAV rep and cap, helper genes, and a rAAV genome. One example of an AAV expression system is the triple transfection method.

The term "terminal repeat" or "TR" includes any viral terminal repeat or synthetic sequence that forms a hairpin structure and functions as an inverted terminal repeat (i.e., mediates the desired functions such as replication, virus packaging, integration and/or provirus rescue, and the like). The ITR can be an AAV ITR or a non-AAV ITR. For example, a non-AAV ITR sequence such as those of other parvoviruses (e.g., canine parvovirus, bovine parvovirus, mouse parvovirus, porcine parvovirus, human parvovirus B-19) or the SV40 hairpin that serves as the origin of SV40 replication can be used as an ITR, which can further be modified by truncation, substitution, deletion, insertion and/or addition. Further, the ITR can be partially or completely synthetic, such as the "double-D sequence" as described in U.S. Pat. No. 5,478,745 to Samulski et al.

AAV genomes have palindromic sequences at both their 5' and 3' ends. The palindromic nature of the sequences leads to the formation of a hairpin structure that is stabilized by the formation of hydrogen bonds between the complementary base pairs. This hairpin structure is believed to adopt a "Y" or a "T" shape. See, e.g., FIELDS et al. VIROLOGY, volume 2, chapters 69 & 70 (4th ed., Lippincott-Raven Publishers).

An "AAV inverted terminal repeat" or "AAV ITR" may be from any AAV, including but not limited to serotypes 1, 2, 3a, 3b, 4, 5, 6, 7, 8, 9, 10, 11, or 13, snake AAV, avian AAV, bovine AAV, canine AAV, equine AAV, ovine AAV, goat AAV, shrimp AAV, or any other AAV now known or later discovered (see, e.g., Table 1). An AAV ITR need not have the native terminal repeat sequence (e.g., a native AAV ITR sequence may be altered by insertion, deletion, truncation and/or missense mutations), as long as the terminal repeat mediates the desired functions, e.g., replication, virus packaging, integration, and/or provirus rescue, and the like.

The virus vectors of the invention can further be "targeted" virus vectors (e.g., having a directed tropism) and/or a "hybrid" AAV (i.e., in which the viral ITRs and viral capsid are from different AAV or other parvoviruses) as described in international patent publication WO 00/28004 and Chao et al., *Mol. Therapy* 2:619 (2000). In other embodiments, the virus vectors are "chimeric" AAV (i.e., in which the capsid proteins are from more than one serotype and/or the capsid proteins are modified to contain sequences from more than one serotype).

Further, the viral capsid or genomic elements can contain other modifications, including insertions, deletions and/or substitutions.

The term "template" or "substrate" is used herein to refer to a polynucleotide sequence that may be replicated to produce the AAV viral DNA. For the purpose of vector production, the template will typically be embedded within a larger nucleotide sequence or construct, including but not limited to a plasmid, naked DNA vector, bacterial artificial chromosome (BAC), yeast artificial chromosome (YAC) or a viral vector (e.g., adenovirus, herpesvirus, Epstein-Barr Virus, AAV, baculoviral, retroviral vectors, and the like). Alternatively, the template may be stably incorporated into the chromosome of a packaging cell.

As used herein, AAV "Rep coding sequences" indicate the nucleic acid sequences that encode the AAV non-structural proteins that mediate viral replication and the production of new virus particles. The AAV replication genes and proteins have been described in, e.g., FIELDS et al. VIROLOGY, volume 2, chapters 69 & 70 (4th ed., Lippincott-Raven Publishers).

The "Rep coding sequences" need not encode all of the AAV Rep proteins. For example, with respect to AAV, the Rep coding sequences do not need to encode all four AAV Rep proteins (Rep78, Rep68, Rep52 and Rep40), in fact, it is believed that AAV5 only expresses the spliced Rep68 and Rep40 proteins. In representative embodiments, the Rep coding sequences encode at least those replication proteins that are necessary for viral genome replication and packaging into new virions. The Rep coding sequences will generally encode at least one large Rep protein (i.e., Rep78/68) and one small Rep protein (i.e., Rep52/40). In particular embodiments, the Rep coding sequences encode the AAV Rep78 protein and the AAV Rep52 and/or Rep40 proteins. In other embodiments, the Rep coding sequences encode the Rep68 and the Rep52 and/or Rep40 proteins. In a still further embodiment, the Rep coding sequences encode the Rep68 and Rep52 proteins, Rep68 and Rep40 proteins, Rep78 and Rep52 proteins, or Rep78 and Rep40 proteins.

As used herein, the term "large Rep protein" refers to Rep68 and/or Rep78. Large Rep proteins may be either wild-type or synthetic. A wild-type large Rep protein may be from any AAV, including but not limited to serotypes 1, 2, 3a, 3b, 4, 5, 6, 7, 8, 9, 10, 11, or 13, or any other AAV now known or later discovered (see, e.g., Table 1). A synthetic large Rep protein may be altered by insertion, deletion, truncation and/or missense mutations.

Those skilled in the art will further appreciate that it is not necessary that the replication proteins be encoded by the same polynucleotide. For example, the AAV p19 promoter may be inactivated and the large Rep protein(s) expressed from one polynucleotide and the small Rep protein(s) expressed from a different polynucleotide. Typically, however, it will be more convenient to express the replication proteins from a single construct. In some systems, the viral promoters (e.g., AAV p19 promoter) may not be recognized by the cell, and it is therefore necessary to express the large and small Rep proteins from separate expression cassettes. In other instances, it may be desirable to express the large Rep and small Rep proteins separately, i.e., under the control of separate transcriptional and/or translational control elements. For example, it may be desirable to control expression of the large Rep proteins, so as to decrease the ratio of large to small Rep proteins. In the case of insect cells, it may be advantageous to down-regulate expression of the large Rep proteins (e.g., Rep78/68) to avoid toxicity to the cells (see, e.g., Urabe et al., *Hum. Gene Ther.* 13:1935 (2002)).

As used herein, the AAV "cap coding sequences" encode the structural proteins that form a functional AAV capsid (i.e., can package DNA and infect target cells). Typically, the cap coding sequences will encode all of the AAV capsid subunits, but less than all of the capsid subunits may be encoded as long as a functional capsid is produced. Typically, but not necessarily, the cap coding sequences will be present on a single nucleic acid molecule. The capsid structure of AAV is described in more detail in BERNARD N. FIELDS et al., VIROLOGY, volume 2, chapters 69 & 70 (4th ed., Lippincott-Raven Publishers).

As used herein, the term "animal component-free" refers to a culture medium or other composition that does not contain any product extracted or purified from animals or animal cells, including serum, enzymes, carbohydrates, nucleic acids, proteins, antibodies, extracellular matrix, etc.

Suspension HEK293 Cell Line

In an effort to generate a scalable manufacturing technology to produce high titer and highly pure rAAV, an HEK293 cell line was developed that grows under animal component-free suspension conditions. The cell line was developed from a qualified master cell bank. After adaption to growth in animal component-free suspension conditions, the suspension HEK293 cell line maintained its ability for efficient transfection and rAAV production.

Thus, one aspect of the invention relates to an isolated HEK293 cell which was deposited under the Budapest Treaty with the ATCC, P.O. Box 1549, Manassas, Va., 20108, on Oct. 24, 2012 (ATCC Deposit No. PTA 13274).

In one embodiment, the cell line is suitable for culturing in any volume of culture medium, from 10 ml (e.g., in shaker flasks) to 10 L, 50 L, 100 L, or more (e.g., in bioreactors). The cell line is suitable for production of all serotypes, chimeras, and hybrids of AAV, e.g., AAV1, AAV2, AAV3, AAV4, AAV5, AAV6, AAV7, AAV8, AAV9, AAV10, AAV11, AAV12, AAV13, and any chimeras and/or hybrids thereof, e.g., AAV1-13 2.5, 2i8, 9.45 and other chimeric or hybrid capsids.

In certain embodiments, the cell line can be used in an AAV production method that provides at least about $4\times10^4$ vector genome-containing particles per cell prior to purification, e.g., at least about $1\times10^5$ vector genome-containing particles per cell prior to purification. In other embodiments, the cell line can be used in an AAV production method that provides at least about $1\times10^{12}$ purified vector genome-containing particles per liter of cell culture, e.g., at least about $1\times10^{13}$ or $1\times10^{14}$ purified vector genome-containing particles per liter of cell culture.

Methods of Producing Virus Vectors

The present invention further provides methods of producing virus vectors. In one aspect, the invention relates to a method of producing AAV particles, comprising: (a) providing to the HEK293 cells of the invention an AAV expression system; (b) culturing the cells under conditions in which AAV particles are produced; and (c) optionally isolating the AAV particles. In one embodiment, the cells are cultured in suspension. In another embodiment, the cells are cultured in animal component-free conditions. The animal component-free medium can be any animal component-free medium (e.g., serum-free medium) compatible with HEK293 cells. Examples include, without limitation, SFM4Transfx-293 (Hyclone), Ex-Cell 293 (JRH Biosciences), LC-SFM (Invitrogen), and Pro293-S (Lonza).

Conditions sufficient for the replication and packaging of the AAV particles can be, e.g., the presence of AAV sequences sufficient for replication of an AAV template and encapsidation into AAV capsids (e.g., AAV rep sequences and AAV cap sequences) and helper sequences from adenovirus and/or herpesvirus. In particular embodiments, the AAV template comprises two AAV ITR sequences, which are located 5' and 3' to the heterologous nucleic acid sequence, although they need not be directly contiguous thereto.

In some embodiments, the AAV template comprises an ITR that is not resolved by Rep to make duplexed AAV vectors as described in international patent publication WO 01/92551.

The AAV template and AAV rep and cap sequences are provided under conditions such that virus vector comprising the AAV template packaged within the AAV capsid is produced in the cell. The method can further comprise the step of collecting the virus vector from the culture. In one embodiment, the virus vector can be collected by lysing the cells, e.g., after removing the cells from the culture medium, e.g., by pelleting the cells. In another embodiment, the virus vector can be collected from the medium in which the cells are cultured, e.g., to isolate vectors that are secreted from the cells. Some or all of the medium can be removed from the culture one time or more than one time, e.g., at regular intervals during the culturing step for collection of rAAV (such as every 12, 18, 24, or 36 hours, or longer extended time that is compatible with cell viability and vector production), e.g., beginning about 48 hours post-transfection. After removal of the medium, fresh medium, with or without additional nutrient supplements, can be added to the culture. In one embodiment, the cells can be cultured in a perfusion system such that medium constantly flows over the cells and is collected for isolation of secreted rAAV. Collection of rAAV from the medium can continue for as long as the transfected cells remain viable, e.g., 48, 72, 96, or 120 hours or longer post-transfection. In certain embodiments, the collection of secreted rAAV is carried out with serotypes of AAV (such as AAV8 and AAV9), which do not bind or only loosely bind to the producer cells. In other embodiments, the collection of secreted rAAV is carried out with heparin binding serotypes of AAV (e.g., AAV2) that have been modified so as to not bind to the cells in which they are produced. Examples of suitable modifications, as well as rAAV collection techniques, are disclosed in U.S. Publication No. 2009/0275107, which is incorporated by reference herein in its entirety.

The AAV replication and capsid sequences may be provided by any method known in the art. Current protocols typically express the AAV rep/cap genes on a single plasmid. The AAV replication and packaging sequences need not be provided together, although it may be convenient to do so. The AAV rep and/or cap sequences may be provided by any viral or non-viral vector. For example, the rep/cap sequences may be provided by a hybrid adenovirus or herpesvirus vector (e.g., inserted into the E1a or E3 regions of a deleted adenovirus vector). EBV vectors may also be employed to express the AAV cap and rep genes. One advantage of this method is that EBV vectors are episomal, yet will maintain a high copy number throughout successive cell divisions (i.e., are stably integrated into the cell as extra-chromosomal elements, designated as an "EBV based nuclear episome," see Margolski, Curr. Top. Microbiol. Immun. 158:67 (1992)).

As a further alternative, the rep/cap sequences may be stably incorporated into a cell.

Typically the AAV rep/cap sequences will not be flanked by the TRs, to prevent rescue and/or packaging of these sequences.

The AAV template can be provided to the cell using any method known in the art. For example, the template can be supplied by a non-viral (e.g., plasmid) or viral vector. In particular embodiments, the AAV template is supplied by a herpesvirus or adenovirus vector (e.g., inserted into the E1a or E3 regions of a deleted adenovirus). As another illustration, Palombo et al., J. Virol. 72:5025 (1998), describes a baculovirus vector carrying a reporter gene flanked by the AAV TRs. EBV vectors may also be employed to deliver the template, as described above with respect to the rep/cap genes.

In another representative embodiment, the AAV template is provided by a replicating rAAV virus. In still other embodiments, an AAV provirus comprising the AAV template is stably integrated into the chromosome of the cell.

To enhance virus titers, helper virus functions (e.g., adenovirus or herpesvirus) that promote a productive AAV infection can be provided to the cell. Helper virus sequences necessary for AAV replication are known in the art. Typically, these sequences will be provided by a helper adenovirus or herpesvirus vector. Alternatively, the adenovirus or herpesvirus sequences can be provided by another non-viral or viral vector, e.g., as a non-infectious adenovirus miniplasmid that carries all of the helper genes that promote efficient AAV production as described by Ferrari et al., *Nature Med.* 3:1295 (1997), and U.S. Pat. Nos. 6,040,183 and 6,093,570.

Further, the helper virus functions may be provided by a packaging cell with the helper sequences embedded in the chromosome or maintained as a stable extrachromosomal element. Generally, the helper virus sequences cannot be packaged into AAV virions, e.g., are not flanked by TRs.

Those skilled in the art will appreciate that it may be advantageous to provide the AAV replication and capsid sequences and the helper virus sequences (e.g., adenovirus sequences) on a single helper construct. This helper construct may be a non-viral or viral construct. As one nonlimiting illustration, the helper construct can be a hybrid adenovirus or hybrid herpesvirus comprising the AAV rep/cap genes.

In one particular embodiment, the AAV rep/cap sequences and the adenovirus helper sequences are supplied by a single adenovirus helper vector. This vector can further comprise the AAV template. The AAV rep/cap sequences and/or the AAV template can be inserted into a deleted region (e.g., the E1a or E3 regions) of the adenovirus.

In a further embodiment, the AAV rep/cap sequences and the adenovirus helper sequences are supplied by a single adenovirus helper vector. According to this embodiment, the AAV template can be provided as a plasmid template.

In another illustrative embodiment, the AAV rep/cap sequences and adenovirus helper sequences are provided by a single adenovirus helper vector, and the AAV template is integrated into the cell as a provirus. Alternatively, the AAV template is provided by an EBV vector that is maintained within the cell as an extrachromosomal element (e.g., as an EBV based nuclear episome).

In a further exemplary embodiment, the AAV rep/cap sequences and adenovirus helper sequences are provided by a single adenovirus helper. The AAV template can be provided as a separate replicating viral vector. For example, the AAV template can be provided by an AAV particle or a second recombinant adenovirus particle.

According to the foregoing methods, the hybrid adenovirus vector typically comprises the adenovirus 5' and 3' cis sequences sufficient for adenovirus replication and packaging (i.e., the adenovirus terminal repeats and PAC sequence). The AAV rep/cap sequences and, if present, the AAV template are embedded in the adenovirus backbone and are flanked by the 5' and 3' cis sequences, so that these sequences may be packaged into adenovirus capsids. As described above, the adenovirus helper sequences and the AAV rep/cap sequences are generally not flanked by TRs so that these sequences are not packaged into the AAV virions.

Zhang et al., *Gene Ther.* 18:704 ((2001)) describe a chimeric helper comprising both adenovirus and the AAV rep and cap genes.

Herpesvirus may also be used as a helper virus in AAV packaging methods. Hybrid herpesviruses encoding the AAV Rep protein(s) may advantageously facilitate scalable AAV vector production schemes. A hybrid herpes simplex virus type I (HSV-1) vector expressing the AAV-2 rep and cap genes has been described (Conway et al., *Gene Ther.* 6:986 (1999) and WO 00/17377).

AAV vector stocks free of contaminating helper virus may be obtained by any method known in the art. For example, AAV and helper virus may be readily differentiated based on size. AAV may also be separated away from helper virus based on affinity for a heparin substrate (Zolotukhin et al. *Gene Ther.* 6:973 (1999)). Deleted replication-defective helper viruses can be used so that any contaminating helper virus is not replication competent. As a further alternative, an adenovirus helper lacking late gene expression may be employed, as only adenovirus early gene expression is required to mediate packaging of AAV. Adenovirus mutants defective for late gene expression are known in the art (e.g., ts100K and ts149 adenovirus mutants).

In representative embodiments, the method of the invention is completely scalable, so it can be carried out in any desired volume of culture medium, e.g., from 10 ml (e.g., in shaker flasks) to 10 L, 50 L, 100 L, or more (e.g., in bioreactors such as wave bioreactor systems and stirred tanks).

The method is suitable for production of all serotypes and chimeras of AAV, e.g., AAV1, AAV2, AAV3, AAV4, AAV5, AAV6, AAV7, AAV8, AAV9, AAV10, AAV11, AAV12, AAV13, and any chimeras thereof.

In certain embodiments, the method provides at least about $1 \times 10^4$ vector genome-containing particles per cell prior to purification, e.g., at least about $2 \times 10^4$, $3 \times 10^4$, $4 \times 10^4$, $5 \times 10^4$, $6 \times 10^4$, $7 \times 10^4$, $8 \times 10^4$, $9 \times 10^4$, or $1 \times 10^5$ or more vector genome-containing particles per cell prior to purification. In other embodiments, the method provides at least about $1 \times 10^{12}$ purified vector genome-containing particles per liter of cell culture, e.g., at least about $5 \times 10^{12}$, $1 \times 10^{13}$, $5 \times 10^{13}$, or $1 \times 10^{14}$ or more purified vector genome-containing particles per liter of cell culture.

Recombinant Virus Vectors

The virus vectors produced by the present invention are useful for the delivery of nucleic acids to cells in vitro, ex vivo, and in vivo. In particular, the virus vectors can be advantageously employed to deliver or transfer nucleic acids to animal, including mammalian, cells.

Any heterologous nucleic acid sequence(s) of interest may be delivered in the virus vectors produced by the present invention. Nucleic acids of interest include nucleic acids encoding polypeptides or RNAs, including reporter, therapeutic (e.g., for medical or veterinary uses), immunogenic (e.g., for vaccines), or diagnostic polypeptides or RNAs.

As a further alternative, the heterologous nucleic acid can encode any polypeptide or RNA that is desirably produced in a cell in vitro, ex vivo, or in vivo. For example, the virus vectors may be introduced into cultured cells and the expressed gene product isolated therefrom.

It will be understood by those skilled in the art that the heterologous nucleic acid(s) of interest can be operably associated with appropriate control sequences. For example, the heterologous nucleic acid can be operably associated with expression control elements, such as transcription/translation control signals, origins of replication, polyadenylation signals, internal ribosome entry sites (IRES), promoters, and/or enhancers, and the like.

Those skilled in the art will appreciate that a variety of promoter/enhancer elements can be used depending on the level and tissue-specific expression desired. The promoter/enhancer can be constitutive or inducible, depending on the pattern of expression desired. The promoter/enhancer can be native or foreign and can be a natural or a synthetic sequence. By foreign, it is intended that the transcriptional initiation region is not found in the wild-type host into which the transcriptional initiation region is introduced.

In particular embodiments, the promoter/enhancer elements can be native to the target cell or subject to be treated. In representative embodiments, the promoters/enhancer element can be native to the heterologous nucleic acid sequence. The promoter/enhancer element is generally chosen so that it functions in the target cell(s) of interest. Further, in particular embodiments the promoter/enhancer element is a mammalian promoter/enhancer element. The promoter/enhancer element may be constitutive or inducible.

Inducible expression control elements are typically advantageous in those applications in which it is desirable to provide regulation over expression of the heterologous nucleic acid sequence(s). Inducible promoters/enhancer elements for gene delivery can be tissue-specific or -preferred promoter/enhancer elements, and include muscle specific or preferred (including cardiac, skeletal and/or smooth muscle specific or preferred), neural tissue specific or preferred (including brain-specific or preferred), eye specific or preferred (including retina-specific and cornea-specific), liver specific or preferred, bone marrow specific or preferred, pancreatic specific or preferred, spleen specific or preferred, and lung specific or preferred promoter/enhancer elements. Other inducible promoter/enhancer elements include hormone-inducible and metal-inducible elements. Exemplary inducible promoters/enhancer elements include, but are not limited to, a Tet on/off element, a RU486-inducible promoter, an ecdysone-inducible promoter, a rapamycin-inducible promoter, and a metallothionein promoter.

In embodiments wherein the heterologous nucleic acid sequence(s) is transcribed and then translated in the target cells, specific initiation signals are generally included for efficient translation of inserted protein coding sequences. These exogenous translational control sequences, which may include the ATG initiation codon and adjacent sequences, can be of a variety of origins, both natural and synthetic.

The virus vectors produced according to the present invention provide a means for delivering heterologous nucleic acids into a broad range of cells, including dividing and non-dividing cells. The virus vectors can be employed to deliver a nucleic acid of interest to a cell in vitro, e.g., to produce a polypeptide in vitro or for ex vivo gene therapy. The virus vectors are additionally useful in a method of delivering a nucleic acid to a subject in need thereof, e.g., to express an immunogenic or therapeutic polypeptide or a functional RNA. In this manner, the polypeptide or functional RNA can be produced in vivo in the subject. The subject can be in need of the polypeptide because the subject has a deficiency of the polypeptide. Further, the method can be practiced because the production of the polypeptide or functional RNA in the subject may impart some beneficial effect.

The virus vectors can also be used to produce a polypeptide of interest or functional RNA in cultured cells or in a subject (e.g., using the subject as a bioreactor to produce the polypeptide or to observe the effects of the functional RNA on the subject, for example, in connection with screening methods).

Having described the present invention, the same will be explained in greater detail in the following examples, which are included herein for illustration purposes only, and which are not intended to be limiting to the invention.

Example 1

Materials and Methods

Derivation of Suspension HEK293 Cells from an Adherent HEK293 Qualified Master Cell Bank.

The derivation of the suspension cell line from the parental HEK293 Master Cell Bank (MCB), was performed in a Class 10,000 clean room facility. The derivation of the suspension cell line was carried out in a two phase process that involved first weaning the cells off of media containing bovine serum and then adapting the cells to serum free suspension media compatible with HEK293 cells. The suspension cell line was created as follows. First, a vial of qualified Master Cell Bank (MCB) was thawed and placed into culture in DMEM media containing 10% fetal bovine serum (FBS) and cultured for several days to allow the cells to recover from the freeze/thaw cycle. The MCB cells were cultured and passaged over a 4 week period while the amount of FBS in the tissue culture media was gradually reduced from 10% to 2.5%. The cells were then transferred from DMEM 2.5% FBS into serum free suspension media and grown in shaker flasks. The cells were then cultured in the serum-free media for another 3 weeks while their growth rate and viability was monitored. The adapted cells were then expanded and frozen down. A number of vials from this cell bank were subsequently thawed and used during process development studies to create a scalable manufacturing process using shaker flasks and wave bioreactor systems to generate rAAV vectors. Suspension HEK293 cells were grown in serum-free suspension media that supports both growth and high transfection efficiency in shaker flasks and wave bioreactor bags. Multitron Shaker Incubators (ATR) were used for maintenance of the cells and generation of rAAV vectors at specific rpm shaking speeds (based on cell culture volumes), 80% humidity, and 5% $CO_2$.

Transfection of Suspension HEK293 Cells.

On the day of transfection, the cells were counted using a ViCell XR Viability Analyzer (Beckman Coulter) and diluted for transfection. To mix the transfection cocktail the following reagents were added to a conical tube in this order: plasmid DNA, OPTIMEM® I (Gibco) or OptiPro SFM (Gibco), or other serum free compatible transfection media, and then the transfection reagent at a specific ratio to plasmid DNA. The pXR series of helper plasmids were used in these studies to generate multiple rAAV serotype vectors (Rabinowitz et al., *J. Virol.* 76:791 (2002)). The cocktail was inverted to mix prior to being incubated at RT. The transfection cocktail was then pipetted into the flasks and placed back in the shaker/incubator. All optimization studies were carried out at 30 mL culture volumes followed by validation at larger culture volumes. Cells were harvested 48 hours post-transfection.

Production of rAAV Using Wave Bioreactor Systems.

Wave bags were seeded 2 days prior to transfection. Two days post-seeding the wave bag, cell culture counts were taken and the cell culture was then expanded/diluted before transfection. The wave bioreactor cell culture was then transfected. Cell culture was harvested from the wave bioreactor bag at least 48 hours post-transfection.

Analyzing Transfection Efficiency/GFP Expression Using Flow Cytometry.

Approximately 24 hours post-transfection, 1 mL of cell culture was removed from each flask or wave bioreactor bag as well as an untransfected control. Samples were analyzed using a Dako Cyan flow cytometer.

Harvesting Suspension Cells from Shaker Flasks and Wave Bioreactor Bags.

48 hours post-transfection, cell cultures were collected into 500 mL polypropylene conical tubes (Corning) either by pouring from shaker flasks or pumping from wave bioreactor bags. The cell culture was then centrifuged at 655×g for 10 min using a Sorvall RC3C plus centrifuge and H6000A rotor. The supernatant was discarded, and the cells were resuspended in 1×PBS, transferred to a 50 mL conical tube, and centrifuged at 655×g for 10 min. At this point, the pellet could either be stored in NLT-60° C. or continued through purification.

Titering rAAV from Cell Lysate Using qPCR.

10 mL of cell culture was removed and centrifuged at 655×g for 10 min using a Sorvall RC3C plus centrifuge and H6000A rotor. The supernatant was decanted from the cell pellet. The cell pellet was then resuspended in 5 mL of DNase buffer (5 mM $CaCl_2$, 5 mM $MgCl_2$, 50 mM Tris-HCl pH 8.0) followed by sonication to lyse the cells efficiently. 300 µL was then removed and placed into a 1.5 mL microfuge tube. 140 units of DNase I was then added to each sample and incubated at 37° C. for 1 hour. To determine the effectiveness of the DNase digestion, 4-5 µg of TReGFP plasmid was spiked into a non-transfected cell lysate with and without the addition of DNase. 50 µL of EDTA/Sarkosyl solution (6.3% sarkosyl, 62.5 mM EDTA pH 8.0) was then added to each tube and incubated at 70° C. for 20 minutes. 50 µL of Proteinase K (10 mg/mL) was then added and incubated at 55° C. for at least 2 hours. Samples were then boiled for 15 minutes to inactivate the Proteinase K. An aliquot was removed from each sample to be analyzed by qPCR. Two qPCR reactions were carried out in order to effectively determine how much rAAV vector was generated per cell. One qPCR reaction was set up using a set of primers designed to bind to a homologous sequence on the backbones of plasmids XX680, pXR2 and TReGFP. The second qPCR reaction was set up using a set of primers to bind and amplify a region within the eGFP gene. qPCR was conducted using Sybr green reagents and Light cycler 480 from Roche. Samples were denatured at 95° C. for 10 minutes followed by 45 cycles (90° C. for 10 sec, 62° C. for 10 sec and 72° C. for 10 sec) and melting curve (1 cycle 99° C. for 30 sec, 65° C. for 1 minute continuous).

Purification of rAAV from Crude Lysate.

Each cell pellet was adjusted to a final volume of 10 mL. The pellets were vortexed briefly and sonicated for 4 minutes at 30% yield in one second on, one second off bursts. After sonication, 550 U of DNase was added and incubated at 37° C. for 45 minutes. The pellets were then centrifuged at 9400×g using the Sorvall RCSB centrifuge and HS-4 rotor to pellet the cell debris and the clarified lysate was transferred to a Type70Ti centrifuge tube (Beckman 361625). In regard to harvesting and lysing the suspension HEK293 cells for isolation of rAAV, one skilled in the art could use mechanical methods such as microfluidization or chemical methods such as detergents, etc. followed by a clarification step using depth filtration or Tangential Flow Filtration (TFF).

AAV Vector Purification.

Clarified AAV lysate was purified by column chromatography methods as one skilled in the art would be aware of and described in the following manuscripts (Allay et al., Davidoff et al., Kaludov et al., Zolotukhin et al., Zolotukin et al, etc).

Titering rAAV Using Dot Blot.

100 µL, of DNase buffer (140 units DNase, 5 mM $CaCl_2$, 5 mM $MgCl_2$, 50 mM Tris-HCl pH 8.0) was added to each well of a 96-well microtiter plate. 1-3 µL or serial dilutions of virus was added to each well and incubated at 37° C. for 30 min. The samples were then supplemented with 15 µL Sarkosyl/EDTA solution (6.3% sarkosyl, 62.5 mM EDTA pH 8.0) and placed at 70° C. for 20 min. Next, 15 µL of Proteinase K (10 mg/mL) was added and incubated at 50° C. for at least 2 hours. 125 µL of NaOH buffer (80 mM NaOH, 4 mM EDTA pH 8.0) was added to each well. A series of transgene specific standards were created through a dilution series. NaOH buffer was then added and incubated. Nylon membrane was incubated at RT in 0.4 M Tris-HCl, pH 7.5 and then set up on dot blot apparatus. After a 10-15 minute incubation in NaOH buffer, the samples and standards were loaded into the dot blot apparatus onto the GeneScreen PlusR hybridization transfer membrane (PerkinElmer). The sample was then applied to the membrane using a vacuum. The nylon membrane was soaked in 0.4 M Tris-HCl, pH 7.5 and then cross linked using UV strata linker 1800 (Stratagene) at 600 ujouls×100. The membrane was then prehybridized in CHURCH buffer (1% BSA, 7% SDS, 1 mM EDTA, 0.5 M $Na_3PO_4$, pH 7.5). After pre-hybridization, the membrane was hybridized overnight with a $^{32}$P-CTP labeled transgene probe (Roche Random Prime DNA labeling kit). The following day, the membrane was washed with low stringency SSC buffer (1×SSC, 0.1% SDS) and high stringency (0.1×SSC, 0.1% SDS). It was then exposed on a phosphorimager screen and analyzed for densitometry using a STORM840 scanner (GE).

Analyzing rAAV Vector Purity Using Silver Stain Method.

Samples from purified vector were loaded onto NuPage 10% Bis-Tris gels (Invitrogen) and run using 1× NuPage running buffer. Typically, 1×10$^{10}$ particles were loaded per well. The gels were treated with SilverXpress Silver staining kit #LC6100 (Invitrogen).

Analysis of Self-Complementary Genomes Using Alkaline Gel Electrophoresis and Southern Blot.

Briefly, purified self-complementary rAAV was added to 200 µL of DNase I buffer (140 units DNase, 5 mM $CaCl_2$, 5 mM $MgCl_2$, 50 mM Tris-HCl pH 8.0) and incubated at 37° C. for 60 minutes, followed by inactivation of the DNase by adding 30 µL of EDTA Sarkosyl/EDTA solution (6.3% sarkosyl, 62.5 mM EDTA pH 8.0) and placed at 70° C. for 20 min. 20 µL of Proteinase K (10 mg/mL) was then added to the sample and incubated for a minimum of 2 hours at 50° C. Phenol/Chloroform was added in a 1:1 ratio, followed by ethanol precipitation of the viral vector DNA. The pelleted DNA was then resuspended in alkaline buffer (50 mM NaOH, 1 mM EDTA) for denaturation, loaded onto a 1% alkaline agarose gel, and run at 25V overnight. The gel was then equilibrated in alkaline transfer buffer (0.4 M NaOH, 1 M NaCl) and a southern blot was performed via an overnight transfer of the vector DNA to a GeneScreen PlusR hybridization transfer membrane (PerkinElmer). The membrane was then neutralized using 0.5 M Tris pH 7.5 with 1 M NaCl, and was hybridized overnight with a $^{32}$P-CTP labeled transgene probe. After washing the membrane as previously described, the membrane was exposed to a phosphorimager screen and analyzed using a STORM840 scanner.

Transduction Assays.

HeLaRC-32 cells (Chadeuf et al., *J. Gene Med.* 2:260 (2000)) were plated at 2×10$^5$ cells/well of a 24 well plate and incubated at 37° C. overnight. The cells were observed for 90-100% confluence. 50 mL of DMEM with 2% FBS, 1% Pen/Strep was pre-warmed, and adenovirus (dl309) was added at a MOI of 10. The dl309 containing media was aliquoted in 900 µL fractions and used to dilute the rAAV in a series of ten-fold dilutions. The rAAV was then plated at 400 µL and allowed to incubate for 48 hours at 37° C. For rAAV containing the eGFP transgene, the GFP positive cells were counted using fluorescence microscopy. For rAAV containing the Luciferase transgene, the media was aspirated from the cells and 100 µL of passive lysis buffer was added. The cells were frozen at −80° C. and then thawed at 37° C. to aid in cell lysis. 50 µL of the cell lysate was then pipetted into an opaque 96 well plate along with 50 µL of luciferin. The cells were then read on a Wallac plate reader for relative light units.

Concentration Assays.

The starting vector stock was sampled and loaded onto a vivaspin column and centrifuged at 470×g (Sorvall H1000B) in 10 minute intervals. Once the desired volume/concentration had been achieved, both sides of the membrane were rinsed with the retentate, which was then harvested. Samples of the pre-concentrated and concentrated rAAV were taken to determine physical titers and transducing units.

Transmission Electron Microscopy (TEM) of Negatively Stained rAAV Particles.

Electron microscopy allows a direct visualization of the viral particles. Purified dialyzed rAAV vectors were placed on a 400-mesh glow-discharged carbon grid by inversion of the grid on a 20 µL drop of virus. The grid was then washed 2 times by inversion on a 20 µL drop of ddH$_2$O followed by inversion of the grid onto a 20 µL drop of 2% uranyl acetate for 30 seconds. The grids are blotted dry by gently touching Whatman paper to the edges of the grids. Each vector was visualized using a Zeiss EM 910 electron microscope.

Example 2

Development of a Suspension HEK293 Cell Line

The purpose of this work was to generate a scalable manufacturing technology to produce high titer and highly pure rAAV using transient transfection technology and mammalian HEK293 cells. To begin, an adherent HEK293 cell line from our qualified master cell bank was adapted to grow in animal component-free and antibiotic-free suspension conditions as described in Example 1. After adaptation to animal component-free suspension conditions and selection of a compatible animal component-free suspension medium, the suspension HEK293 cell line maintained its ability for efficient transfection and rAAV production.

Example 3

Optimization of Transfection Conditions

Two of the major requirements for production of rAAV using transient transfection are determining the optimal plasmid ratios of the three plasmids and the transfection reagent to total DNA ratio. The transfection reagent can be chemical based (e.g., calcium phosphate or polyethyleneimine) or biological/lipid based (e.g., 293fectin, lipofectamine, etc.). The suspension HEK293 cells were initially grown in serum free media-1 in a 30 mL volume in 125 mL shaker flasks on the day of transfection. Various ratios of XX680:Rep/Cap:TReGFP were tested with transfection reagent to DNA ratios of 2:1 and 4:1 with 1 µg DNA/mL of cells and incubated at room temperature. As shown in FIG. 1A, the plasmid ratio of 2:1.5:1 with a transfection reagent to DNA ratio of 2:1 generated the most vector genomes (vg)/cell. Vg/cell from cell lysates were determined using qPCR methods as described in Example 1. It was evident that the transfection reagent to DNA ratio of 4:1 generated the least amount of vg/cell at all plasmid ratios tested. This was most likely due to a lower cell viability post-transfection detected by the Beckman ViCell XR Viability analyzer, suggesting a level of toxicity was reached with the transfection reagent. In addition, the 4:1 transfection reagent to DNA ratio led to larger cell aggregates after transfection.

A number of commercially available transfection protocols describe the importance of the transfection cocktail volume and how it can influence transfection efficiency. To determine how transfection cocktail volume affects these cells, transfection cocktail volumes of 2, 5 and 10% were selected. The % volume is based on the final cell culture volume in the shaker flask. For example, 30 mL cultures were used to determine the optimal transfection cocktail volume so for a 10% transfection cocktail, 27 mL of cell culture was placed in the shaker flask and the transfection cocktail was 3 mL. As illustrated in FIG. 1B, a 5% transfection cocktail volume was shown to have the better transfection efficiency (based on GFP flow cytometry) and generated the most vg/cell.

Example 4

Optimization of Cell Density and Plasmid DNA Concentrations

Figure 2:
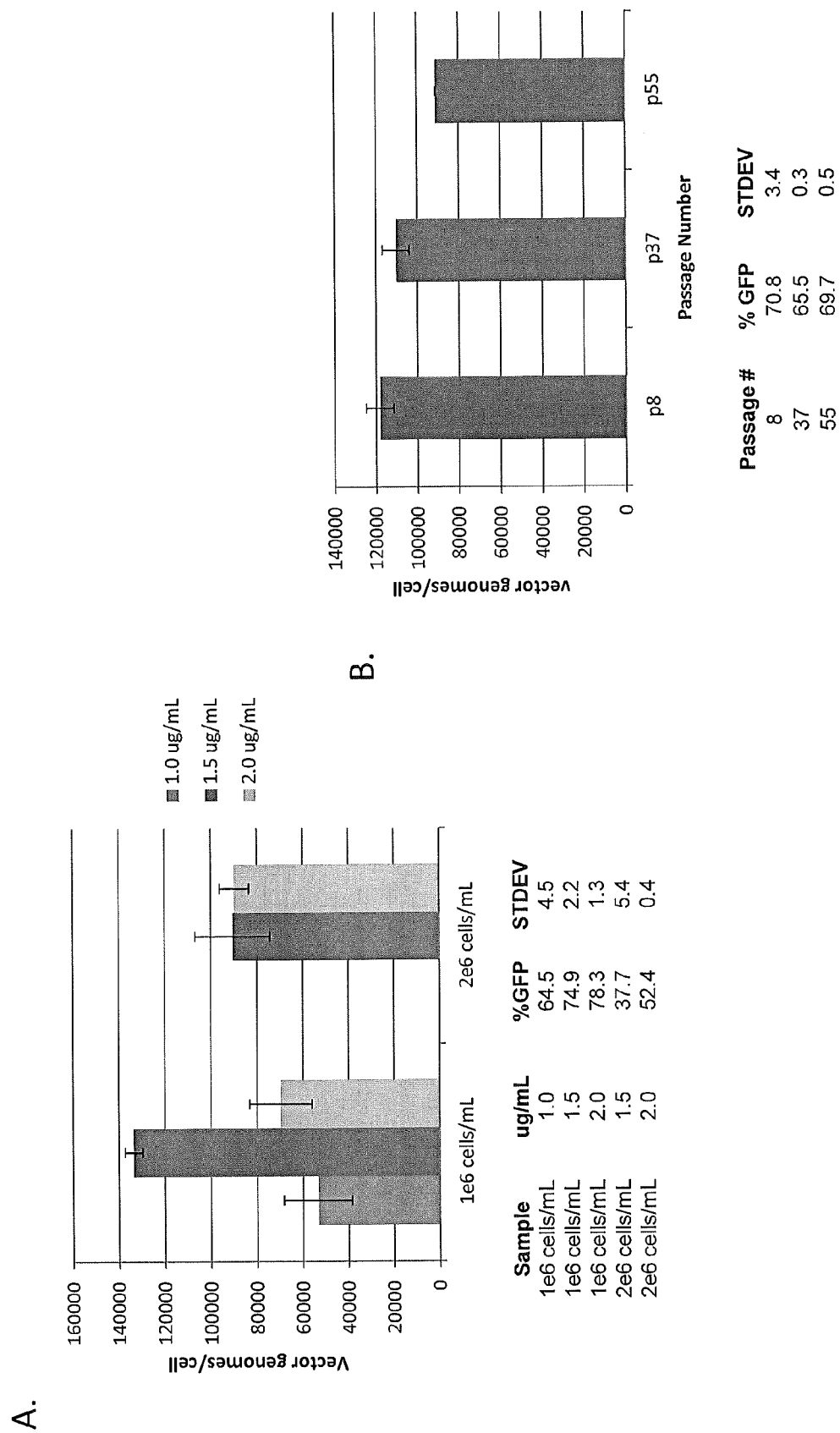
FIGS. 2A-2B show cell density transfection optimization experiments and the impact of cell culture age on vector production. (A) $1 \times 10^6$ and $2 \times 10^6$ viable cells/mL were transfected with 1 to 2 μg of plasmid DNA (2:1.5:1 XX680: AAV rep/cap helper:TR plasmid). (B) Low, medium and high passage cells were transfected using optimized parameters to determine if cell culture age impacted transfection efficiency and rAAV production.

Prior to initiating these studies, we began using another serum-free media (serum-free media-2) that supported better growth, increased transfection efficiency and increased vector production/cell (see Table 2). The suspension HEK293 cells were diluted in the serum-free media-2 to 1×10$^6$ and 2×10$^6$ viable cells/mL to achieve a final cell culture volume of 30 mL. 1, 1.5 and 2 µg/mL of plasmid DNA were utilized in this set of experiments. Based on the data shown in FIG. 2A, it was evident that the rAAV vector production was best when the cell density was at 1×10$^6$ viable cells/mL at the time of transfection using 1.5 µg/mL of plasmid DNA.

TABLE 2

| Samples | GFP % 24 hr | Total vector yield | Vg/cell |
| --- | --- | --- | --- |
| Serum-free media-1 | 45.7 | 1.27 × 10$^{12}$ | 4.2 × 10$^4$ |
| Serum-free media-2 | 73.6 | 6.50 × 10$^{12}$ | 2.2 × 10$^5$ |

The suspension HEK293 cells were passaged a number of times and when low, medium and high passage cells were available, they were transfected to determine if cell culture age impacted transfection efficiency and rAAV production. As shown in FIG. 2B, transfection efficiency is not impacted by cell culture age, but rAAV production per cell decreases over time suggesting that the suspension HEK293 cell clone that was developed should be used a maximum of 30-40 passages.

Example 5

Purification of rAAV Serotypes Using Column Chromatography

Figure 3B:
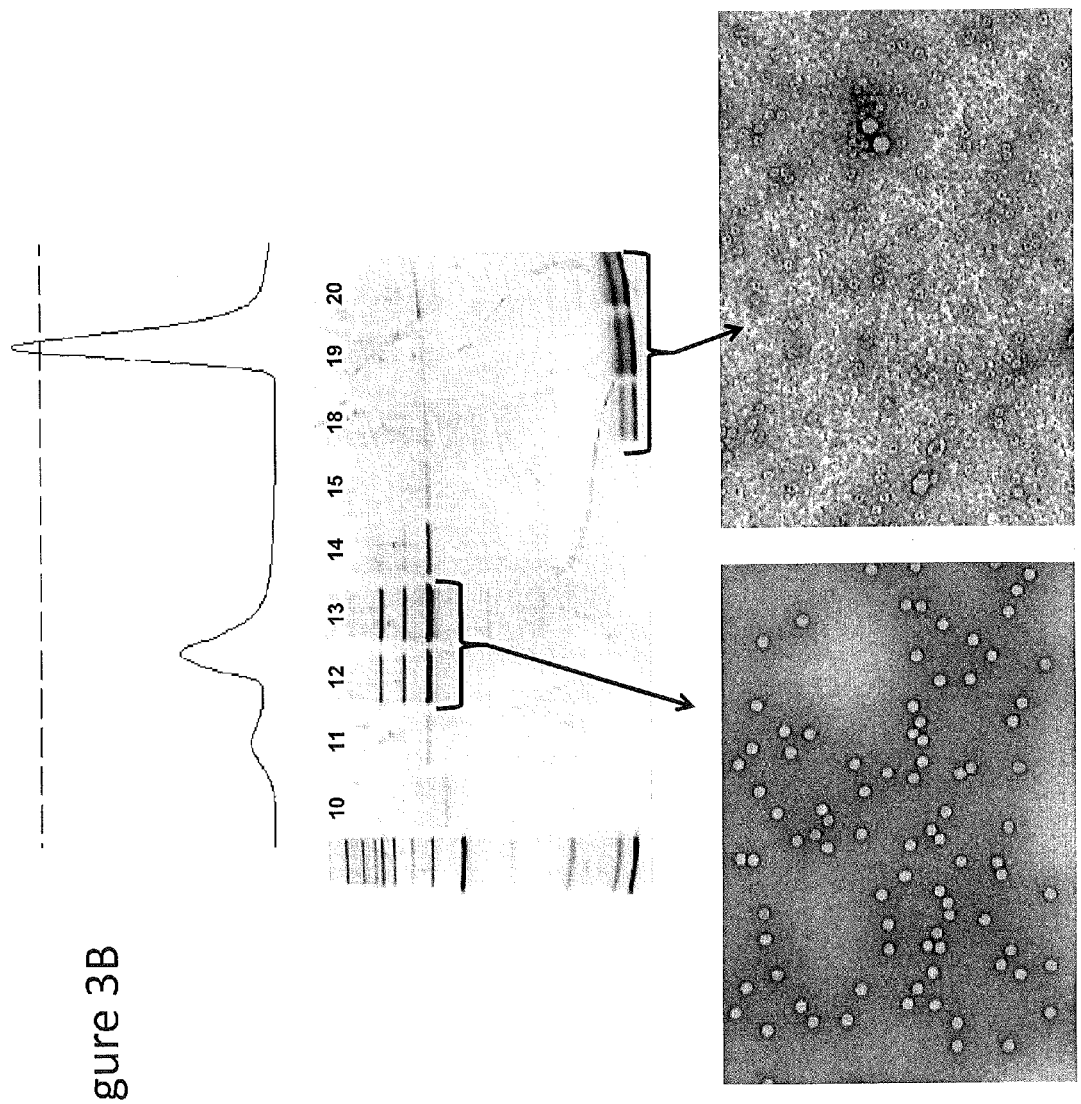

In conjunction with the optimization of rAAV production in suspension HEK293 cells, it was decided that another focus should be AAV purification. It was desired to develop a universal purification strategy for all AAV serotypes. Previous studies reported that purification of several different serotypes could be accomplished through the use of column chromatography. It was rationalized that column chromatography could therefore be used to purify all serotypes through modulation of specific parameters during the binding and elution steps. As illustrated in FIG. 3, highly pure elution fractions are collected utilizing column chromatography methods. This universal protocol was used to purify all AAV serotypes and chimeric capsids.

Example 6

Production and Purification of Single-Stranded and Self-Complementary rAAV Serotypes 1-6, 8 and 9

Figure 4:
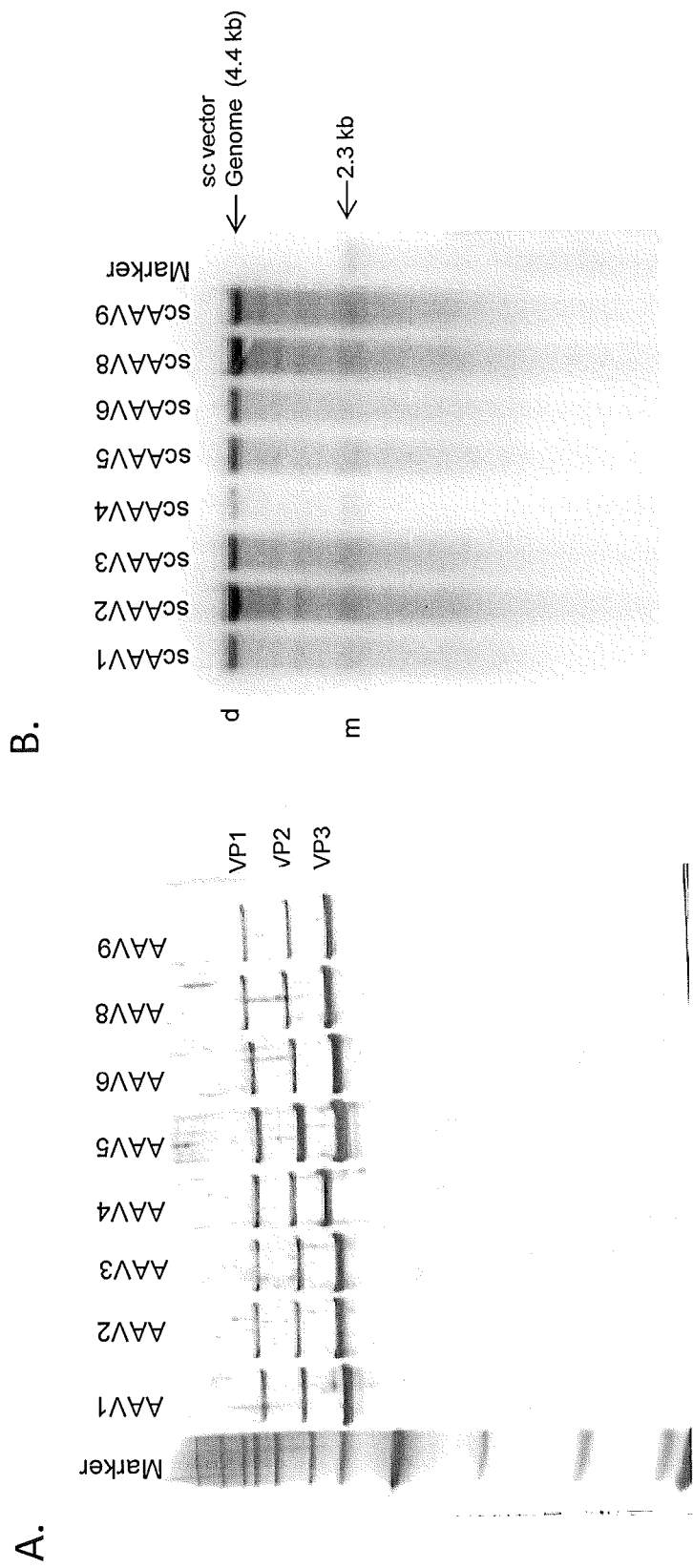
FIGS. 4A-4B demonstrate production and purification of single-stranded and self-complementary rAAV serotypes 1-6, 8 and 9 using optimized production and purification conditions. One liter of cell culture in a shaker flask was transfected for each serotype. Cell lysate and post-purification titers were calculated for each serotype in addition to the vg:TU ratio using HeLaRC32 cells (see methods). (A) Silver stain image of single-stranded serotypes 1-6, 8 and 9 post-purification. (B) Southern blot of self-complementary rAAV1-6, 8 and 9. Vector genomes were isolated from each serotype capsid and run on an alkaline agarose gel.

As described in Example 1, 1 liter culture volumes were transfected using the optimized transfection parameters to generate single-stranded and self-complementary rAAV serotypes 1-6, 8 and 9 packaging CMV-GFP transgene cassettes. As shown in Table 3, the transfection efficiency (based on GFP flow cytometry) was nearly equivalent among all transfections. All of the serotypes packaging a single-stranded genome generated around and above $1 \times 10^5$ vg/cell. Excluding rAAV4, all single-stranded rAAV serotypes tested generated $8.2 \times 10^{12}$ to $3.3 \times 10^{13}$ total rAAV from 1 liter of cell culture post-purification and were relatively free of any proteins other than VP1, VP2, and VP3 as depicted in the silver stain in FIG. 4A. It is well known that self-complementary vector preps yield less total vector containing particles than their single-stranded counterparts and are usually comprised of varying concentrations of both self-complementary (dimer) and single-stranded (monomer) genomes (McCarty et al., *Gene Ther.* 8:1248 (2001)). Again excluding rAAV4, all self-complementary rAAV serotypes tested generated $4.0 \times 10^{12}$ to $1.3 \times 10^{13}$ total rAAV from 1 liter of cell culture post-purification. As shown in FIG. 4B, the rAAV particles efficiently packaged a high percentage of self-complementary genomes. When additional self-complementary rAAV vectors were generated with various transgene cassettes a majority of the genomes packaged were self-complementary indicating that these results are not exclusive to self-complementary GFP cassettes.

A universal cell line that is permissive to most AAV serotypes has not been found. However, a modified HeLa cell line coined HeLaRC-32 (Chadeuf et al., *J. Gene Med.* 2:260 (2000)) can be transduced in various degrees by all serotypes tested. The cell line contains an integrated AAV2 rep and cap gene and upon infection with adenovirus (dl309), any vector gene flanked by AAV2 ITRs will be replicated. The increased genome copy number will elicit a more robust expression of the gene of interest, in this case GFP, which can then be visualized and counted using fluorescence microscopy. Transducing units (TU) are then calculated based upon the dilution and multiplying the average number of counts/field by the total number of fields per well at the specific magnification. It is apparent in Table 3 that a range of vg:TU ratios exists between serotypes which is most likely due to the range of permissiveness of HeLaRC-32 cells for each serotype. This could be at the level of binding and entry and/or trafficking within the cell. These transduction experiments were repeated several times and transduction to particle ratios remained consistent. Therefore, transduction assays such as this or similar to this can only be used as a guide or measuring tool to qualitatively determine whether a specific rAAV serotype prep falls within a specific acceptance criteria set by the investigator. As expected, the self-complementary rAAV vectors were more infectious than the single-stranded rAAV vectors. As described in Aucoin et al., comparison of transduction or infectivity data between publications should be done with vigilance due to the variety of assays employed to quantitate infectivity (Aucoin et al., *Biotechnol. Adv.* 26:73 (2008)).

TABLE 3

| Vector | Transfection Efficiency (%) | Lysate vg/cell* | Total vg/L post-purification | Vg: TU |
|---|---|---|---|---|
| AAV1 CMV-GFP | 73.8 | $9.7 \times 10^4$ | $1.3 \times 10^{13}$ | 45 |
| AAV2 CMV-GFP | 71.2 | $2.1 \times 10^5$ | $3.3 \times 10^{13}$ | 155 |
| AAV3 CMV-GFP | 74.5 | $1.1 \times 10^5$ | $1.1 \times 10^{13}$ | 8 |
| AAV4 CMV-GFP | 75.6 | $8.9 \times 10^4$ | $2.8 \times 10^{12}$ | 14684 |
| AAV5 CMV-GFP | 74.3 | $1.9 \times 10^5$ | $2.8 \times 10^{13}$ | 137 |
| AAV6 CMV-GFP | 73.6 | $5.7 \times 10^4$ | $8.2 \times 10^{12}$ | 17 |
| AAV8 CMV-GFP | 74.4 | $1.9 \times 10^5$ | $3.3 \times 10^{13}$ | 716 |
| AAV9 CMV-GFP | 73.0 | $2.1 \times 10^5$ | $2.2 \times 10^{13}$ | 1350 |
| scAAV1 CMV-GFP | 78.5 | $4.2 \times 10^4$ | $5.3 \times 10^{12}$ | 15 |
| scAAV2 CMV-GFP | 76.6 | $1.1 \times 10^5$ | $1.4 \times 10^{13}$ | 88 |
| scAAV3 CMV-GFP | 79.9 | $6.5 \times 10^4$ | $7.4 \times 10^{12}$ | 9 |
| scAAV4 CMV-GFP | 78.2 | $4.8 \times 10^4$ | $1.0 \times 10^{12}$ | 9605 |
| scAAV5 CMV-GFP | 76.6 | $9.3 \times 10^4$ | $8.7 \times 10^{12}$ | 50 |
| scAAV6 CMV-GFP | 77.5 | $6.1 \times 10^4$ | $4.0 \times 10^{12}$ | 11 |
| scAAV8 CMV-GFP | 78.2 | $1.1 \times 10^5$ | $1.3 \times 10^{13}$ | 651 |
| scAAV9 CMV-GFP | 76.4 | $1.2 \times 10^5$ | $1.2 \times 10^{13}$ | 936 |

Figure 5:
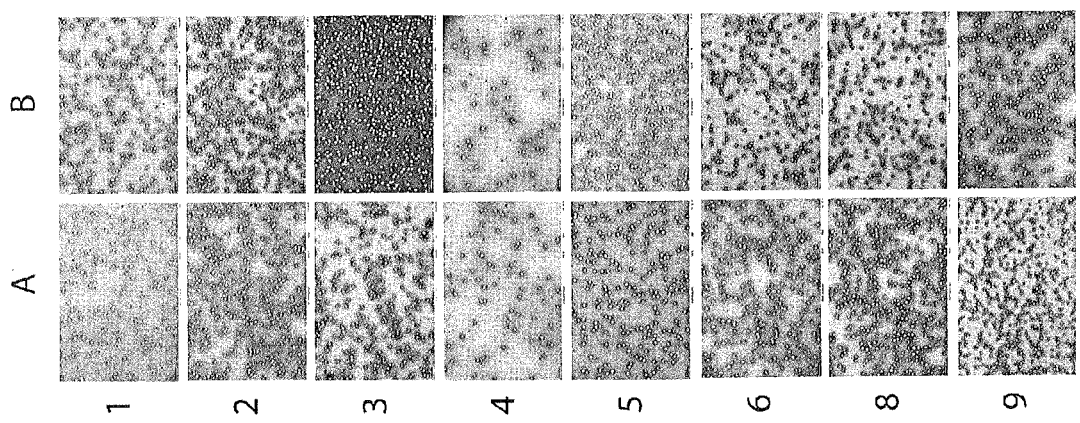
FIG. 5 shows negative stain TEM images of single-stranded and self-complementary rAAV serotypes 1-6, 8 and 9. Full to empty capsid ratios for each serotype were determined based on negative stain TEM images.

To confirm overall purity of the single-stranded and self-complementary rAAV, each serotype was imaged using negative stain transmission electron microscopy (TEM) (FIG. 5). It is well known that a large number of empty particles are generated when producing rAAV in any of the current production technologies. Discovering procedures that will effectively remove the empty particles from full particles is needed. Negative stain TEM is one of a couple of methods for determining the ratio of empty to full particles. Empty particles take up the negative stain (2% uranyl acetate) differently than the full particles making it possible to quantitate the number of full and empty particles in a vector preparation. The other is an ELISA-based method, which utilizes a capsid specific antibody that recognizes both full and empty particles. qPCR or dot blot titers are then subtracted from the total particle titer generated from the ELISA to determine the empty to full capsid ratio. Capsid antibodies for most AAV serotypes have yet to be established and characterized for use in an ELISA. As depicted in the table included in FIG. 5, the overall full to empty particle ratio was no less than 10, suggesting that the purification process effectively removes empty particles. The negative stain TEM images were also utilized to determine the effectiveness of the final storage solution to prevent aggregation of the rAAV particles. It is clear that the final storage buffer is capable of preventing aggregation of the rAAV particles, which will most likely impact infectivity and spread of vector when delivered in vivo.

Example 7

Figure 6:
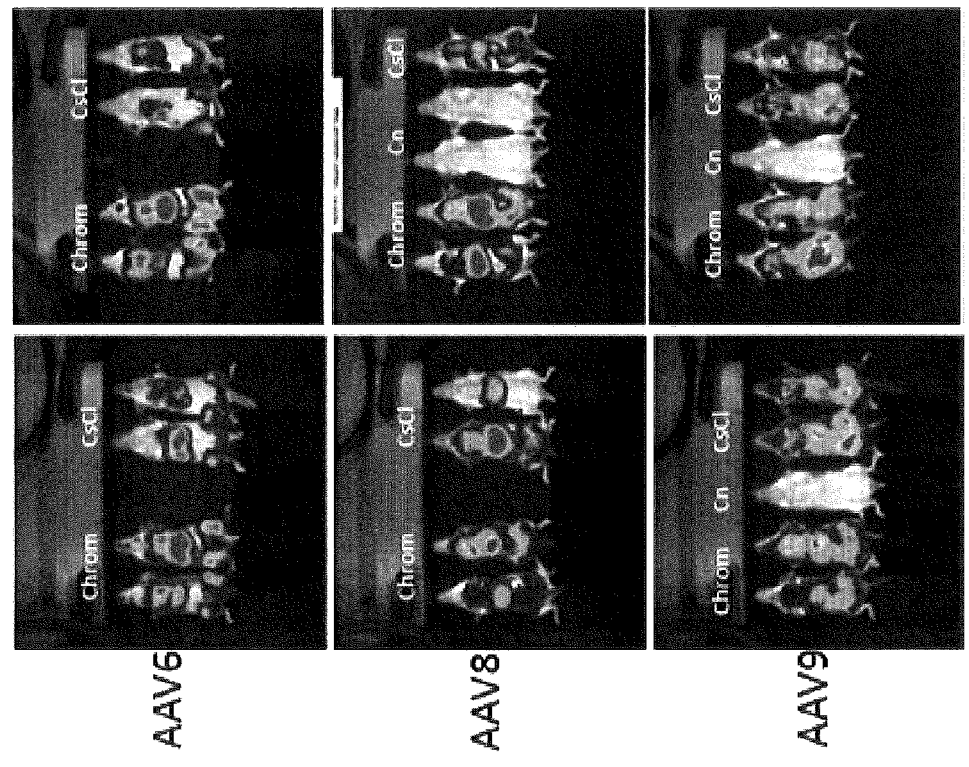
FIG. 6 shows in vivo images of mice injected with $1 \times 10^{11}$ vg of AAV6, 8, and 9 CBA-Luc vectors. The CBA-Luciferase vectors were administered into each mouse via tail vein injection. CBA-Luc vectors generated from suspension HEK293 cells were purified via discontinuous density gradient/column chromatography and those generated from adherent HEK293 cells were purified via CsCl density gradients. Mice were imaged at (A) one week and (B) one month. Control mice were injected with PBS. The photon range of AAV8 and 9 was set from $5 \times 10^6$ to $1 \times 10^8$. AAV6 was set from $5 \times 10^4$ to $1 \times 10^6$. The exposure time was 1 minute for AAV8 and 9, and 5 minutes for AAV 6.

In Vivo Comparison of rAAV Generated from Adherent and Suspension HEK293 Cells AAV6, 8 and 9 CBA-Luc vectors were generated using adherent HEK293 cells and suspension HEK293 cells. Vectors produced in adherent cells were purified using CsCl gradients (Grieger et al., Nat. Protoc. 1:1412 (2006)) and the vectors produced in suspension cells were purified using the optimized methods described herein. Prior to in vivo studies, the vectors were titered on the same dot blot. HeLaRC32 cells were infected with serial dilutions of each vector and gene expression was quantitated using a luciferase assay. Based on the in vitro transduction assay, transduction among serotypes was nearly equivalent between purification strategies. $1 \times 10^{11}$ total vg of each serotype CBA-Luc vector was injected into each mouse via tail vein injection. The mice were imaged one week and one month post-injection (FIG. 6). It is clear that the tropism and transduction profiles of each serotype vector tested are similar and are not impacted by the purification methods.

Example 8

Production of rAAV Using Wave Bioreactors

Production parameters for generating rAAV in shaker flasks using animal component-free suspension media were optimized. The next step was to translate the optimized parameters to the wave bioreactor at various cell culture volumes to determine scalability. Table 4 illustrates a number of wave bioreactor runs ranging in size from 4.3 to 10 liters of cell culture generating different serotype vectors. When possible, a 1 liter culture in a shaker flask was transfected to serve as a control to compare transfection efficiency if a GFP vector was produced as well as to compare vector production per liter of culture post-purification. Transfection efficiency was nearly equivalent between flasks and wave bioreactor bags. Interestingly, CMV driven GFP plasmids consistently showed higher percentages of cells expressing GFP than the CBA and mini CBA promoter (CBh) driven GFP plasmids, but generated nearly equivalent yields of vector per liter of culture. This suggests that the transfection efficiency between the CMV and CBA GFP plasmids were similar, but transcription differs between the promoters in HEK293 cells. As was shown in flasks, most wave bioreactor runs generated $1 \times 10^{13}$ purified rAAV vectors per liter of culture establishing that the parameters optimized for transfection and rAAV production in shaker flasks translates to wave bioreactors. In most 10 liter wave bioreactor production runs, greater than $1 \times 10^{14}$ purified scAAV vectors were generated. When factoring in the scale difference, greater than $1 \times 10^{14}$ purified ssAAV would be generated at 10 liter culture volumes in the wave bioreactor (based on AAV2 and AAV9 in Table 4).

TABLE 4

| Vector | Cell culture volume in flask | Cell culture volume in Wave Bioreactor Bag | Transfection efficiency 24 hrs | Total vg yield | Vg/L |
|---|---|---|---|---|---|
| AAV2 CMV-GFP | 1 L | | 78.3% | $2.3 \times 10^{13}$ | $2.3 \times 10^{13}$ |
| | | 5 L | 75.0% | $1.4 \times 10^{14}$ | $2.7 \times 10^{13}$ |
| AAV9 CBA-GFP | 4 L | | 64.6% | $6.7 \times 10^{13}$ | $1.7 \times 10^{13}$ |
| AAV9 CBA-GFP | | 4.3 | 63.4% | $4.3 \times 10^{13}$ | $1.0 \times 10^{13}$ |
| scAAV2i8 CMV GFP | 1 L | | 83.5% | $1.2 \times 10^{13}$ | $1.2 \times 10^{13}$ |
| | | 10 L | 94.1% | $8.8 \times 10^{13}$ | $8.8 \times 10^{12}$ |
| scAAV2i8 CMV Ilc | 8 × 1 L | | | $1.1 \times 10^{14}$ | $1.4 \times 10^{13}$ |
| | | 10 L | | $6.7 \times 10^{13}$ | $6.7 \times 10^{12}$ |
| scAAV9 CMV-GFP | 1 L | | 82.4% | $3.1 \times 10^{13}$ | $3.1 \times 10^{13}$ |
| | | 10 L | 86.7% | $2.0 \times 10^{14}$ | $2.0 \times 10^{13}$ |
| scAAV9 CMV Ilc | 6 × 1 L | | | $2.1 \times 10^{14}$ | $3.5 \times 10^{13}$ |
| | | 10 L | | $3.0 \times 10^{14}$ | $3.0 \times 10^{13}$ |
| | | 10 L | | $2.0 \times 10^{14}$ | $2.0 \times 10^{13}$ |
| scAAV2.5 CBh-GFP | | 8.5 L | 60.3% | $7.2 \times 10^{13}$ | $8.5 \times 10^{12}$ |
| scAAV9 CBh-GFP | | 10 L | 65.2% | $1.4 \times 10^{14}$ | $1.4 \times 10^{13}$ |

Example 9

Concentration of rAAV

Figure 7:
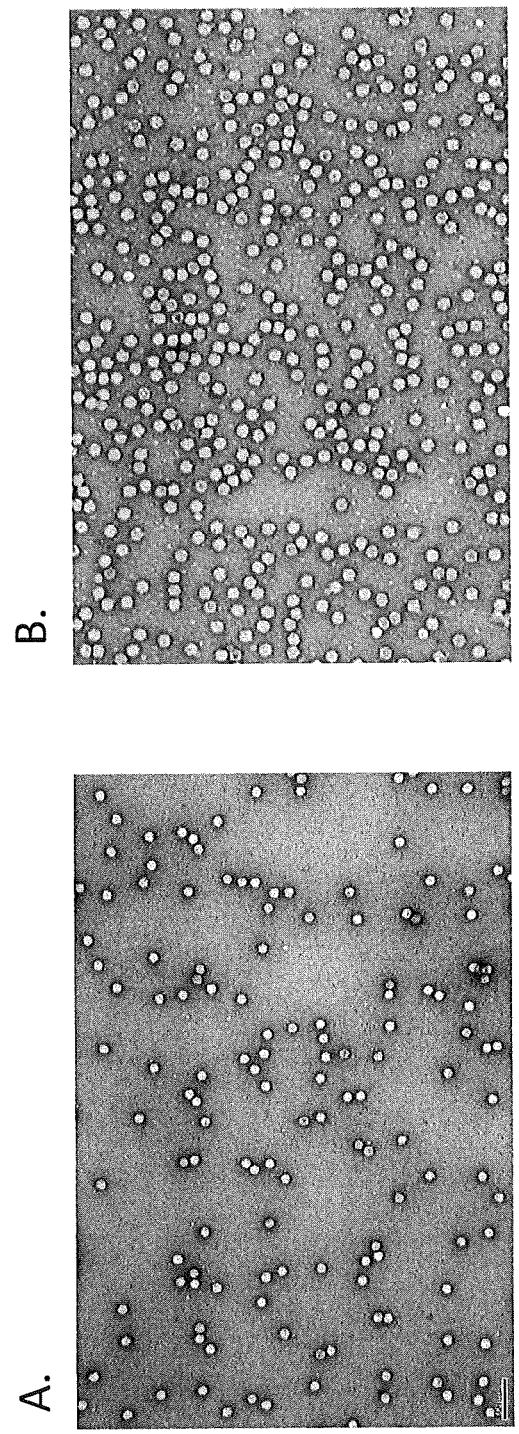
FIGS. 7A-7B show the concentration of single-stranded and self-complementary rAAV vectors post-purification. (A) Negative stain TEM images of pre-concentrated rAAV vector and (B) post-concentrated rAAV vector.

Certain pre-clinical and clinical applications such as direct injections of rAAV into the brain or eye call for low volume/highly concentrated doses of rAAV. Through the use of Sartorius vivaspin columns, specific conditions were optimized that resulted in concentrated rAAV with little to no loss of particle and infectivity as is illustrated in Table 5 (concentration of luciferase vectors; comparison of vector titers and infectivity (luciferase assay) pre and post-concentration) and Table 6 (concentration of GFP vectors; comparison of vector titers and transducing units (HeLaRC32 transduction assay) pre and post-concentration). The columns utilize a PES membrane with a molecular weight cutoff of 100K allowing excess liquid to pass through the filter while retaining the rAAV particles. Various molecular weight cutoff sizes were tested, but were not as effective in retaining and concentrating rAAV. As shown in Tables 5 and 6, an equal titer of the pre-concentrated rAAV was directly measured with an equal titer of the concentrated rAAV. Therefore if a loss in transduction was observed, the relative light units or transducing units for the concentrated rAAV would be less than the pre-concentrated rAAV. After testing several AAV serotypes, there was no significant loss in titer and activity. Thus, the concentrated rAAV had nearly equivalent activity as the pre-concentrated rAAV indicating that the virus was effectively concentrated. To confirm that the viral titer had not changed, total vg and vg/ml were assessed by dot blot. Where total vg remained the same, vg/ml was relative to the volume. It is therefore possible to concentrate rAAV vectors by removing volume via low speed centrifugation utilizing a molecular weight cut off filtration system small enough to retain rAAV. In correlation with the pre-concentration and post-concentration titers, the TEM images in FIGS. 7A and 7B illustrate an increase in vector concentration. The final storage solution is also capable of preventing rAAV particle aggregation at concentrations of $1 \times 10^{13}$ vg/mL.

TABLE 5

| Vector | Sample | Volume (mL) | Infection Volume (μL) | Average RLU | Titer vg/mL | Total VG |
|---|---|---|---|---|---|---|
| AAV5 CBA-Luc | Pre-Conc | 10 | 10 | $1.9 \times 10^4$ | $1.2 \times 10^{11}$ | $1.2 \times 10^{12}$ |
| AAV5 CBA-Luc | Concentrated | 2.2 | 2.2 | $1.8 \times 10^4$ | $7.4 \times 10^{11}$ | $1.6 \times 10^{12}$ |
| AAV6 CBA-Luc | Pre-Conc | 8.8 | 8.8 | $3.5 \times 10^5$ | $3.1 \times 10^{11}$ | $2.7 \times 10^{12}$ |
| AAV6 CBA-Luc | Concentrated | 1 | 1 | $3.7 \times 10^5$ | $3.8 \times 10^{12}$ | $3.8 \times 10^{12}$ |
| AAV9 CBA-Luc | Pre-Conc | 10 | 10 | $4.8 \times 10^4$ | $3.2 \times 10^{11}$ | $3.2 \times 10^{12}$ |
| AAV9 CBA-Luc | Concentrated | 1 | 1 | $5.0 \times 10^4$ | $2.0 \times 10^{12}$ | $2.0 \times 10^{12}$ |
| scAAV2i8 CMV-Ilc | Pre-Conc | 16.6 | | | $3.7 \times 10^{12}$ | $6.1 \times 10^{13}$ |
| scAAV2i8 CMV-Ilc | Concentrated | 6 | | | $9.4 \times 10^{12}$ | $5.6 \times 10^{13}$ |

TABLE 6

| Vector | Sample | Volume (mL) | Titer vg/mL | Total VG | VG/TU Ratio |
|---|---|---|---|---|---|
| scAAV2.5 CBh-GFP | Pre-Conc | 17 | $3.7 \times 10^{12}$ | $6.3 \times 10^{13}$ | 48:1 |
| scAAV2.5 CBh-GFP | Concentrated | 6.5 | $1.2 \times 10^{13}$ | $8.1 \times 10^{13}$ | 57:1 |
| scAAV9 CBh-GFP | Pre-Conc | 22 | $5.8 \times 10^{12}$ | $1.3 \times 10^{14}$ | 2675:1 |
| scAAV9 CBh-GFP | Concentrated | 15 | $9.0 \times 10^{12}$ | $1.4 \times 10^{14}$ | 1246:1 |

Example 10

Continuous rAAV Harvesting from Suspension Media

Figure 9:
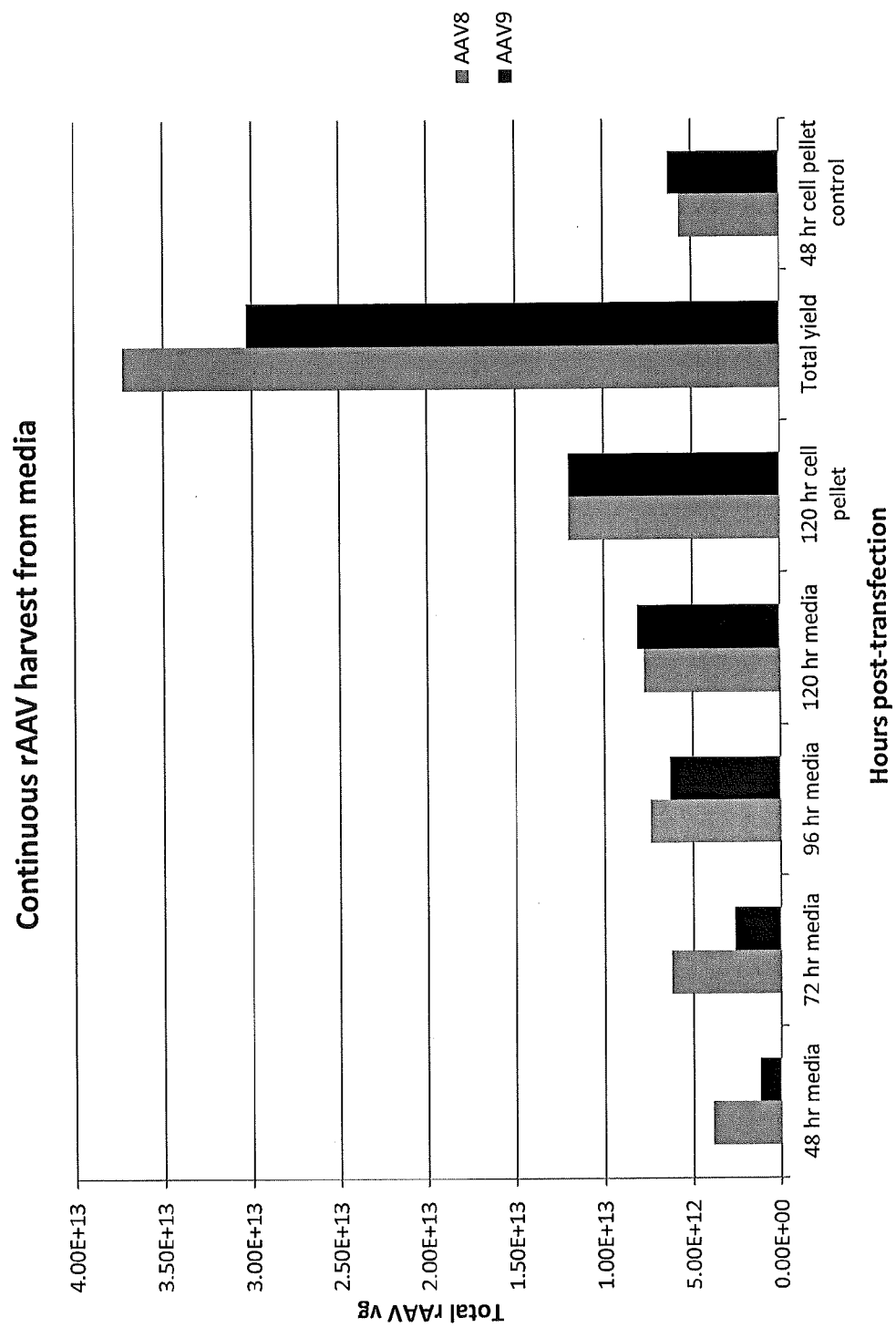
FIG. 9 shows continuous production and harvesting of rAAV8 and rAAV9 from the suspension HEK293 culture medium. Total yield represents all media time-points and 120 hr cell pellet yields added together. 48 hr cell pellet control represents the yield from a standard harvest at 48 hours post-transfection as described herein.

As was described in previous AAV production publications in determining the best time point to harvest AAV from adherent HEK293 cells, it was recently demonstrated when the optimal time point is to harvest AAV from the cell culture media (Lock et al. Hum Gene Ther 21:1259 (2010); Vandenberghe et al. Hum Gene Ther 21:1251 (2010)). To determine if AAV can be collected over time (additively) from the media, we transfected 30 mL cultures of suspension HEK293 cells to produce rAAV8 and rAAV9 CMV-eGFP vectors using the optimized parameters described herein. Forty-eight hours post-transfection, cell cultures were pelleted by low speed centrifugation and the media removed for titering of DNase resistant particles by dot blot and qPCR. The cell pellets were then resuspended in fresh serum-free media and placed back into the shaker incubator for continued growth and production of rAAV. Media samples were then taken every 24 hours and media was replaced every 48 hours. At the 120 hour timepoint, rAAV8 and rAAV9 titers were determined from both the media and cell pellets. As shown in FIG. 9, rAAV8 and rAAV9 can be detected and harvested from the media 48 hours post-transfection with increasing amounts of vector found in the media as time progresses and the media is replaced. When comparing the total yield to the 48 hr cell pellet control in FIG. 9, the continuous harvest method yielded 6.5 and 4.8 fold more rAAV8 and rAAV9 vector, respectively. This is the first report of continuous rAAV harvested from the suspension media at numerous time-points post-transfection using a scalable, animal component-free system. This process was then adapted to bioreactor scale using a 2 L perfusion wave bioreactor bag. 1 L of cell culture was transfected to generate rAAV8 vector. 800 mL of cell culture was removed at each time point (48, 72, 96, 120 and 144 hr) through the perfusion filter within the wave bioreactor bag using a peristaltic pump. 800 mL of fresh animal component-free suspension cell culture media was then added back into the wave bag. Harvested media was then concentrated using TFF followed by clarification and column chromatography purification. Table 7 shows perfusion wave bioreactor rAAV8 vector yields at specific time points (48, 72, 96, 120 and 144 hrs) from cultured media as well as from 144 hr cell pellet. Total purified rAAV8 designates the summation of 48, 72, 96, 120, 144 hr media and 144 hr cell pellet rAAV8 yields. Typical rAAV 48 hr yields represents yield ranges typically achieved for rAAV8 when harvesting from the cell pellet at 48 hours. As shown in Table 7, rAAV8 can be harvested at all time points using the perfusion wave bioreactor bag. Total rAAV8 harvested using the perfusion wave bioreactor bag leads to yields 5-10-fold greater than typical 48 hour cell pellet yields. This is the first report of continuous rAAV harvested from the suspension media using a bioreactor at numerous time-points post-transfection using a scalable animal component free production technology and suspension cells. This will allow the manufacturer to utilize an animal-component free suspension culture to continuously produce, harvest and purify rAAV from the culture media via a single transfection at all scales. This in turn would generate more rAAV from an equal amount of input plasmid than the standard production protocol where the production process is halted when cells are harvested 48-96 hours post-transfection. It would be understood by one skilled in the art that to surpass 144 hours one would need to increase cell viability and to keep vector production consistent among the time points. Depending on AAV helper functions and cell viability one skilled in the art could extend this to the generation of stable cell lines for the generation of rAAV utilizing a regulatable system to turn on and off production based on cell viability and vector yields, etc.

TABLE 7

| Time point (hours) | AAV8 purified |
|---|---|
| 48 | $1.4 \times 10^{13}$ |
| 72 | $2.9 \times 10^{13}$ |
| 96 | $3.0 \times 10^{13}$ |
| 120 | $1.5 \times 10^{13}$ |
| 144 | $9.0 \times 10^{12}$ |
| 144 cell pellet | $8.6 \times 10^{12}$ |
| Total purified AAV8 | $1.1 \times 10^{14}$ |
| Typical AAV8 48 hr yields | $1.0 \times 10^{13}$ to $2.0 \times 10^{13}$ |

A number of Phase I and Phase II clinical trials utilizing AAV have been performed worldwide for inherited and acquired diseases (Aucoin et al., Biotechnol. Adv. 26:73 (2008); Mueller et al., Gene Ther. 15:858 (2008)), The increase in the number of clinical trials emphasizes the need to establish a scalable manufacturing technology that can efficiently generate high titer, highly pure and potent quantities of AAV to meet the expanding clinical demand. A number of approaches to rAAV vector production have been pursued that include packaging cell lines containing the rep and cap genes of AAV, stable proviral cell lines and transient transfection of multiple plasmids into adherent HEK293 cells. Transient transfection of adherent HEK293 cells remains the most widely used method for rAAV production and accounts for most of the rAAV administered in preclinical and clinical applications. The next step was to adapt the transient transfection technology to a scalable technology by transfecting HEK293 cells capable of growing in animal component-free suspension conditions. A few studies have reported rAAV production using suspension HEK293 cells (Durocher et al., *J. Virol. Meth.* 144:32 (2007); Hildinger et al., *Biotechnol. Lett.* 29:1713 (2007); Park et al., *Biotechnol. Bioeng.* 94:416 (2006)), but vector yields (approximately $1.4 \times 10^4$ and $3 \times 10^4$ vg/cell) remain an impediment for the suspension HEK293 cell transient transfection technology.

This disclosure details a robust scalable transient transfection manufacturing technology using a HEK293 cell line that can grow in animal component-free suspension conditions and generate higher rAAV yields per cell than the baculovirus expression vector system and comparable yields per cell to the recent rHSV infection technology. An adherent HEK293 cell clone, selected for high transfection efficiency (>70%) and rAAV vector production was adapted for growth in animal component-free suspension conditions. A number of commercially available serum-free suspension media were screened to select those that supported growth and high transfection efficiency. An animal component-free suspension media was found to support the best growth, high transfection efficiency and high rAAV vector yields (Table 2 and FIGS. 2 and 4). In addition to identifying the optimal media, a number of variables were optimized. Utilizing the optimized parameters, it is possible to generate greater than $1 \times 10^5$ vector genome containing rAAV per cell and greater than $1 \times 10^{13}$ purified vector genome containing rAAV from 1 liter of cell culture media. This was validated from 30 mL to 1 L cell cultures in shaker flasks and up to 10 L volumes in wave bioreactor bags (see Table 3) illustrating that this technology is scalable. In addition, it was shown that rAAV can be continuously harvested from the animal component-free suspension media at various time-points post-transfection using shaker flasks and perfusion wave bioreactor bags significantly increasing overall rAAV yields from an equivalent cell culture volume and input plasmid.

rAAV was purified from cell lysate by using a discontinuous density gradient followed by column chromatography. The load capacity of the discontinuous gradient was optimized to determine the maximum amount of lysate it could effectively clarify (efficient removal of protein contaminants) prior to column chromatography. The column chromatography buffers were optimized to develop a universal purification system to bind and elute all AAV serotypes and chimeric capsids (tested to date) efficiently. Through extensive process development work, it was possible to remove major and minor protein contaminants via simple manipulation of the chromatography buffers without impacting binding and elution profiles of all AAV serotypes and chimeric capsids (reference silver stains in FIGS. 3 and 4). Through a process that is most likely related to the use of discontinuous density gradient and column chromatography, a significant amount of empty particles are removed leaving a high percentage of genome-containing rAAV in the final product (FIG. 5). In summary, the rAAV generated are highly pure, have a high full to empty capsid ratio and have a similar genome to infectivity ratio (based on GFP fluorescence counting assay) to vectors generated using former methods of production (adherent HEK293 cells) and purification (Aucoin et al., *Biotechnol. Adv.* 26:73 (2008)).

Figure 8:
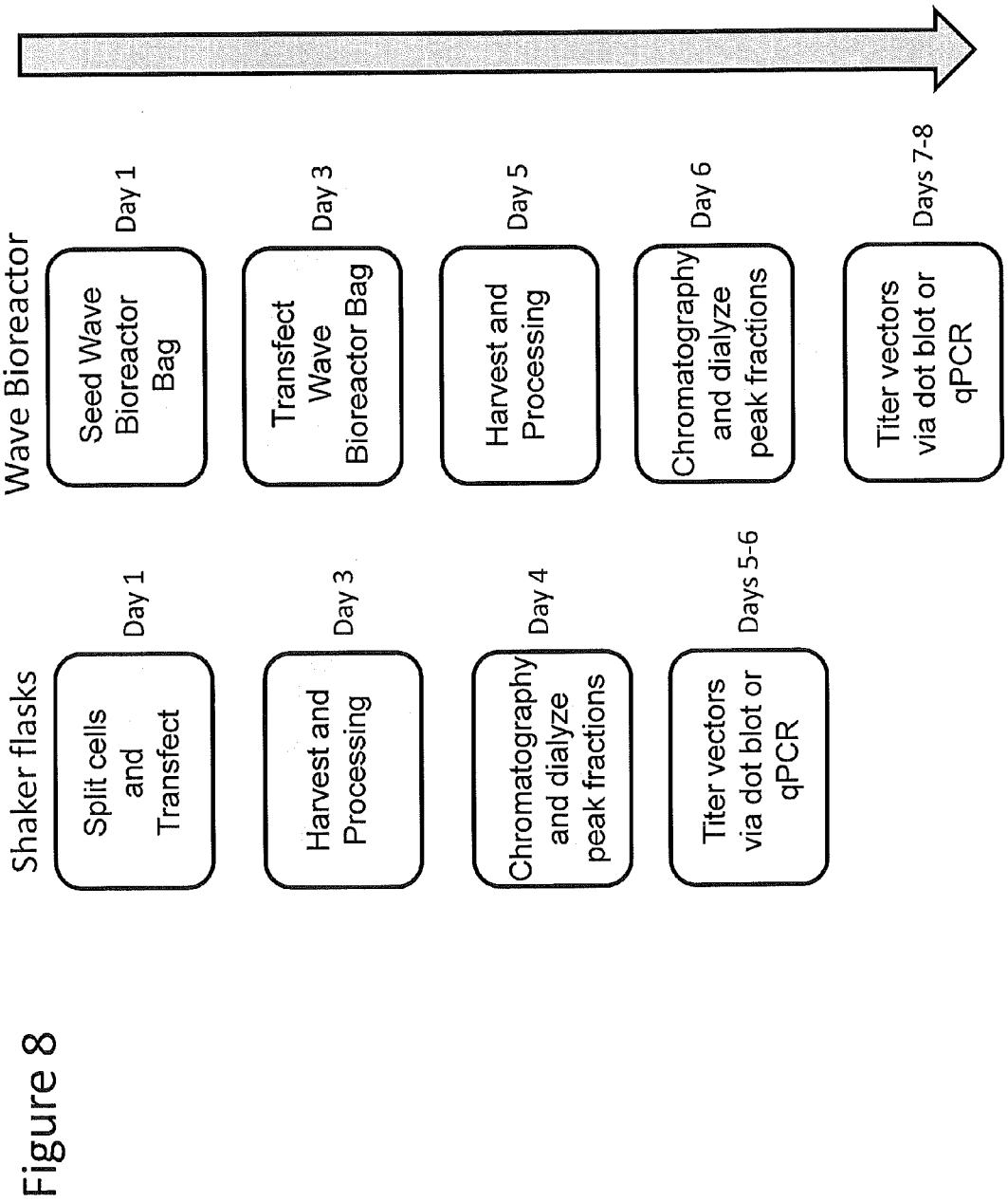
FIG. 8 shows a timeline of rAAV vector production using suspension HEK293 cells grown and transfected in shaker flasks and wave bioreactors.

A number of scalable systems have been developed for the production of rAAV, which include adenovirus-based, rHSV-based, BEVS-based and transient transfection-based methods. In comparison, the present scalable transient transfection technology using suspension HEK293 cells generates more rAAV and more infectious rAAV per cell than adenovirus and BEVS-based rAAV technologies and comparable yields to the rHSV-based production technology. Furthermore, the overall time invested to generate rAAV using this system is nominal (FIG. 8).

The foregoing is illustrative of the present invention, and is not to be construed as limiting thereof. The invention is defined by the following claims, with equivalents of the claims to be included therein.

That which is claimed is:

1. An isolated HEK293 cell deposited as ATCC No. PTA 13274.

* * * * *